(12) United States Patent
Bogoch et al.

(10) Patent No.: US 9,320,784 B2
(45) Date of Patent: Apr. 26, 2016

(54) PEPTIDES SHARED AMONG LETHAL CANCERS AND THERAPEUTIC COMPOSITIONS COMPRISING SAID PEPTIDES

(76) Inventors: Samuel Bogoch, New York, NY (US); Elenore S. Bogoch, New York, NY (US); Anne Elenore Borsanyi, New York, NY (US); Samuel Winston Bogoch, Oakland, CA (US)

( * ) Notice: Subject to any disclaimer, the term of this patent is extended or adjusted under 35 U.S.C. 154(b) by 178 days.

(21) Appl. No.: 13/553,137

(22) Filed: Jul. 19, 2012

(65) Prior Publication Data
US 2013/0084303 A1    Apr. 4, 2013

Related U.S. Application Data

(63) Continuation-in-part of application No. 12/581,112, filed on Oct. 16, 2009, which is a continuation-in-part of application No. 12/538,027, filed on Aug. 7, 2009.

(60) Provisional application No. 61/609,074, filed on Mar. 9, 2012, provisional application No. 61/509,896, filed on Jul. 20, 2011.

(51) Int. Cl.
*C07K 7/08* (2006.01)
*C07K 7/06* (2006.01)
*A61K 39/00* (2006.01)

(52) U.S. Cl.
CPC ............... *A61K 39/0011* (2013.01); *C07K 7/06* (2013.01); *C07K 7/08* (2013.01)

(58) Field of Classification Search
CPC ... A61K 39/00; A61K 39/0011; C07K 14/00; C07K 7/06; C07K 7/08
See application file for complete search history.

(56) References Cited

U.S. PATENT DOCUMENTS

| | | | |
|---|---|---|---|
| 4,132,769 A | 1/1979 | Osther | |
| 4,298,590 A | 11/1981 | Bogoch | |
| 4,486,538 A | 12/1984 | Bogoch | |
| 5,104,854 A | 4/1992 | Schlesinger | |
| 5,231,167 A | 7/1993 | Zanetti | |
| 5,866,690 A | 2/1999 | Bogoch | |
| 6,023,659 A | 2/2000 | Seilhamer | |
| 6,070,126 A | 5/2000 | Kokolus | |
| 6,090,406 A | 7/2000 | Popescu | |
| 6,242,578 B1 | 6/2001 | Bogoch | |
| 6,256,647 B1 | 7/2001 | Toh | |
| 6,470,277 B1 | 10/2002 | Chin | |
| 6,638,505 B2 | 10/2003 | Bogoch | |
| 7,176,275 B2 | 2/2007 | Bogoch | |
| 7,189,800 B2 | 3/2007 | Bogoch | |
| 7,420,028 B2 | 9/2008 | Bogoch | |
| 7,442,761 B2 | 10/2008 | Bogoch | |
| 7,452,963 B2 | 11/2008 | Bogoch | |
| 7,674,880 B2 | 3/2010 | Bogoch | |
| 7,705,129 B2 | 4/2010 | Bogoch | |
| 7,758,863 B2 | 7/2010 | Bogoch | |
| 7,763,705 B2 | 7/2010 | Bogoch | |
| 7,774,144 B2 | 8/2010 | Bogoch | |
| 7,894,999 B2 | 2/2011 | Bogoch | |
| 8,050,871 B2 | 11/2011 | Bogoch | |
| 8,417,462 B2 | 4/2013 | Bogoch | |
| 8,494,781 B2 | 7/2013 | Bogoch | |
| 2002/0120106 A1 | 8/2002 | Bogoch | |
| 2002/0151677 A1 | 10/2002 | Bogoch | |
| 2003/0180328 A1 | 9/2003 | Bogoch | |
| 2003/0194414 A1 | 10/2003 | Bogoch | |
| 2005/0129715 A1 | 6/2005 | Paterson | |
| 2005/0202415 A1 | 9/2005 | Bogoch | |
| 2006/0024669 A1 | 2/2006 | Bogoch | |
| 2007/0026009 A1 | 2/2007 | Bogoch | |
| 2008/0124358 A1* | 5/2008 | Brennan | 424/204.1 |
| 2008/0176217 A1 | 7/2008 | Bogoch | |
| 2008/0241918 A1 | 10/2008 | Sasisekharan | |
| 2008/0260764 A1 | 10/2008 | Bogoch | |
| 2009/0017052 A1 | 1/2009 | Bogoch | |
| 2009/0041795 A1 | 2/2009 | Bogoch | |
| 2009/0269367 A1 | 10/2009 | Bogoch | |

FOREIGN PATENT DOCUMENTS

| | | |
|---|---|---|
| DE | 3628658 A1 | 3/1988 |
| EP | 0 108 564 A1 | 5/1984 |
| WO | 89/07112 | 10/1989 |
| WO | 9632106 | 1/1996 |
| WO | 0018351 | 4/2000 |
| WO | 00/52054 | 10/2000 |
| WO | 0104135 | 1/2001 |
| WO | 02085093 | 10/2002 |
| WO | 03005880 | 1/2003 |
| WO | 0383058 | 10/2003 |
| WO | 2005010032 | 2/2005 |
| WO | 2005004754 | 11/2005 |
| WO | 2006088962 | 8/2006 |
| WO | 2007022151 | 2/2007 |
| WO | 2007149715 | 12/2007 |
| WO | 2008060669 | 5/2008 |
| WO | 2008060702 | 5/2008 |
| WO | 2008121329 | 10/2008 |

(Continued)

OTHER PUBLICATIONS

Gibbs et al. (Nature, 2004, vol. 428. p. 493-521).*

(Continued)

*Primary Examiner* — Agnieszka Boesen
(74) *Attorney, Agent, or Firm* — Daren P. Nicholson

(57) ABSTRACT

The present invention provides cancer peptides related to rapid replication and shared among different histological cancer types. The peptides are provided in compositions for interfering with replication in cancer, in preventive and therapeutic vaccines, and in diagnostic applications. The compositions for interfering with replication in cancer are useful for preventing and treating different histological types of cancer including ectodermic, endodermic, and mesodermic cancers as well as cancers arising in association with HIV.

7 Claims, 1 Drawing Sheet

(56) References Cited

FOREIGN PATENT DOCUMENTS

| WO | 2008/140557 | 11/2008 |
|----|-------------|---------|
| WO | 2008/143717 | 11/2008 |
| WO | 2008/156914 | 12/2008 |
| WO | 2009132209  | 10/2009 |
| WO | 2010/017514 | 2/2010  |
| WO | 2010/123519 | 10/2010 |
| WO | 2013/013075 | 1/2013  |

OTHER PUBLICATIONS

Accession No. F1MAT1_RAT, 2011.*
Carnicki et al. 2005.*
UniProtKB/Swiss-Prot: Q3TUS4, 2005.*
Replikins, Ltd. Press Release, "FluForecast® Replikin Count™ Predicts That the H5N1 Cycle Which Began in 1996 is Now Over" (Feb. 11, 2008).
Replikins, Ltd. Press Release, "Replikins Oral Vaccine Synthesized in 7 days protects 91% of Shrimp Against Lethal Virus" (Mar. 11, 2008).
Replikins, Ltd. Press Release, "H1N1 Influenza Virus with Highest Replikin Count™ Since the 1918 Pandemic Identified in the U.S. and Austria" (Apr. 7, 2008).
Replikins, Ltd. Press Release, "Increases in West Nile Virus Replikin Concentrations Precede Increases in the Number of Human Cases" (May 1, 2008).
Replikins, Ltd. Press Release, "H5N1 Virus Replikin Gene Counts Indicate a New More Virulent Influenza Cycle Has Begun" (Jun. 27, 2008).
Replikins, Ltd. Press Release, "Cancer Mortality Increases with Cancer Cell Replikin Count" (Dec. 4, 2008).
Replikins, Ltd. Press Release, "Rising H9N2 Influenza Replikin Count Has Doubled That of H5N1" (Jan. 15, 2009).
Replikins, Ltd. Press Release, "Confirmation of Bogoch Replikins Influenza Patents by Harvard-CDC and Scripps-Crucell Data" (Mar. 20, 2009).
Replikins, Ltd. Press Release, "Biotechnology Company, Replikins Ltd., Provided Advance Warning of Mexican H1N1 'Swine Flu' Virus Outbreak" (Apr. 25, 2009).
Replikins, Ltd. Press Release, "First H1N1 Swine Flu Vaccine, Replikins-Based, is Ready Now for Testing Worldwide" (May 4, 2009).
Replikins, Ltd. Press Release, Swine Flu (H1N1) Infectivity to Increase Markedly and Lethality to Remain Low According to Latest Replikin Peptide Genomic Data (May 23, 2009).
Replikins, Ltd. Press Release, "Lethality of H1N1 Influenza Virus Increasing According to Latest Replikins Analysis of Virus Peptide Genomic Data" (Jun. 10, 2009).
Replikins, Ltd. Press Release, Latest Replikins Data Predicts Continued High Level of H1N1 (Swine Flu) Infectivity and Lethality (Jul. 28, 2009).
Replikins, Ltd. Press Release, H1N1 Lethality Replikin Count Decreases, Infectivity Remains High (Sep. 30, 2009).
Replikins, Ltd. Press Release, New H1N1 Genomic Data Shows Decrease in Replikin Count of Lethality Gene; Replikin Count of Infectivity Gene Remains High (Sep. 30, 2009).
Replikins, Ltd. Press Release, New Non-Biological Synthetic Replikins™ Vaccines Shown to Be Effective and Fast (Oct. 19, 2009).
Replikins, Ltd. Press Release, Lethality of H1N1 Virus Drops to "Non-Epidemic Resting Levels" in Current Cycle; Virus' Infectivity Remains Increased (Nov. 25, 2009).
Replikins, Ltd. Press Release, Both H5N1 Bird Flu and H1N1 Swine Flu Replikin Counts(TM) are Increasing (Apr. 9, 2010).
Replikins, Ltd. Press Release, Current Severe Outbreaks of Foot and Mouth Disease Predicted by Replikins' BioRadar™ One Year in Advance (Jun. 2009), (Jul. 16, 2010).
Replikins, Ltd. Press Release, New Finding of Rise in H5N1 Virus (Avian Flu) Replikin Count (Oct. 27, 2010).
Replikins, Ltd. Press Release, FAO Warnings Follow Rise in Replikins Count for Both H5N1 and Swine Flu (H1N1); Replikins Synthetic TransFluTM Vaccine Tested (Aug. 31, 2011).
Replikins, Ltd. Press Release, Current H5N1 Flu Outbreak and Location Predicted in 2009 (Feb. 10, 2012).
Replikins, Ltd. Press Release, Discovered Evolution of Genomic Sequences—from Ocean Archaea to Brain Cancer—Leads to New Synthetic Replikin Vaccines for Infectious Diseases and Cancer (Jun. 19, 2012).
Replikins, Ltd. Press Release, Can a Pandemic Be Prevented? (Jul. 30, 2012).
Bogoch et al.,"Genome Replikin Count Predicts Increased Lethality of Cancer [sic Malaria]," Nature Precedings <http://dx.doi.org/10.1038/npre.2012.7143.1> (Apr. 4, 2012).
Bogoch, et al., "Genome Replikin Count Predicts Increased Infectivity/Lethality of Viruses," Nature Precedings <http://dx.doi.org/10.1038/npre2012.7144.1> (Apr. 3, 2012).
PCT International Search Report and Written Opinion, PCT/US2009/061108, Jun. 11, 2010, EPO, Rijswik, NL.
UniProt A8DXX4 (Nov. 13, 2007).
Sui, J et al., "Structural and functional bases for broad-spectrum neutralization of avian and human influenza A viruses," Nature Structural & Molecular Biology, vol. 16 No. 3 (Mar. 2009), published online Feb. 22, 2009; doi:10.1038/nsmb.1566.
Ekiert, D.C. et al, Influenza Virus Epitope Antibody Recognition of a Highly Conserved Influenza Virus Epitope, Science 324, 246 (Apr. 10, 2009) Published online Feb. 26, 2009, 10.1126/science.1171491.
Replikins, Ltd. Press Release, "Highest replikin concentrations and cyclical behavior related to human mortality are found in malaria trypanosomes" (May 19, 2008).
Replikins, Ltd. Press Release, "A new way to predict outbreaks: replikin peptide concentration in H5N1 influenza virus genome as a marker for lethal outbreaks" (Nov. 12, 2008).
Replikins, Ltd. Press Release, "Sitting Ducks" No Longer—Advance Flu Warning Permits Creation of Replikins Custom Synthetic Flu Vaccine in Animals (Nov. 10, 2011).
Ghanem et al., "Peptide-Mediated Interference with Influenza A Virus Polymerase," Journal of Virology 81(14): 7801-7804 (Jul. 2007).
Replikins, Ltd. Press Release, Rising Replikin Counts in E. coli in Germany Since 2005 Preceded Current E. coli Outbreak (Jun. 20, 2011).
PCT International Search Report and Written Opinion, PCT/US2009/053208, Feb. 8, 2010, EPO, Rijswijk, NL.
PCT Invitation to Pay Additional Fees and Communication Relating to the Results of the Partial International Search, PCT/US2009/061108, Mar. 8, 2010, EPO, Rijswijk, NL.
PCT Invitation to Pay Additional Fees and Communication Relating to the Results of the Partial International Search, PCT/US2012/0047451, Oct. 22, 2012, EPO, Rijswijk, NL.
PCT International Search Report and Written Opinion,PCT/US2012/0047451, Jan. 14, 2013, EPO, Rijswik, NL.
Abrams M. B. et al., "Early Detection and Monitoring of Cancer with the Anti-Malignin Antibody Test," Cancer Detection and Prevention, XX, XX, vol. 18, No. 1, 1994, pp. 65-78, XP000673180, ISSN:0361-090X.
Aichele, P. et al., "T Cell Priming T Cell Tolerance Induced by Synthetic Peptides," J. Exp. Med., vol. 182 (Jul. 1995) pp. 261-266.
Bioworld Today, "Anonymous: Other news to note," NLDB [Online] XP002511196, retrieved from STN Database accession No. 2008:64080 abstract Mar. 12, 2008.
Bogoch et al.: In vitro production of the general transformation antibody related to survival in human cancer patients; antimalignin antibody; Abstract, Cancer Detection and Prevention, 1988, vol. 12, Nos. 1-6, pp. 313-320. (Database Medline on STN National Library of Medicine, Bethesda, MD, USA) No. 89028479.
Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.
Bogoch, S. et al., "A Checklist for Suitability of Biomarkers as Surrogate Endpoints in Chemoprevention of Breast Cancer," Journal

(56) References Cited

OTHER PUBLICATIONS of Cellular Biochemistry, Supplement, Boston, US, vol. 19, pp. 173-185, XP009046492, ISSN: 0733-1959, 1994.

Bogoch et al., "Aglyco Pathology of Viral Receptors in Dementias," Annals of the New York Academy of Sciences, New York Academy of Sciences, New York, NY, US, vol. 757, 1995, pp. 413-417, XP008003395, ISSN:0077-8923.

Bogoch et al., "Rapid replication and Replikintm structures: basis of the AMASRTest and CAVAXR," Cancer Detection and Prevention Online, Feb. 9, 2002, XP002350483.

Bogoch et al., "Replikins: The Chemistry of Rapid Replication," Begell House, Inc. NY, NY (2005).

Bogoch, et al., "Prediction of specific virus outbreaks made from the increased concentration of a new class of virus genomic peptides, replikins," Nature Precedings <http://dx.doi:10.1038/npre.2011.6279.1> (Aug. 22, 2011).

Bogoch et al., "Marked Rise in Replikin Counts in H5N1 Influenza Virus Localized to Lethality Gene p B1," Nature Precedings <http://dx.doi.org/10.1038/npre.2011.6420.1> (Sep. 16, 2011).

Bogoch et al., "Replikins Pandemic Prevention: Increase of Strain-Specific Influenza Genomic Replikin Counts, Having Predicted Outbreaks and their Location Seven Times Consecutively, Up to Two Years in Advance, Provides Time for Prevention of Pandemics," Nature Precedings <http://dx.doi.org/10.1038/npre.2012.6952.1> (Mar. 1, 2012).
Bogoch, et al., "Genomic Replikin Counts of Infectious Salmon Anemia Virus (ISAV) in Canada Exceed the Counts in Lethal Outbreaks in Norway, Chile, and Scotland. Real-Time Tracking of the Evolution of the ISAV Genome and the Resultant Replikins Solid Phase ISAV Vaccine Make ISAV Pandemic Prevention Possible," Nature Precedings <http://dx.doi.org/10.1038/npre.2012.6991.1> (Mar. 15, 2012).
Bogoch, et al., "Genome Replikin Count Predicts Increased Lethality of Resistant Tuberculosis," Nature Precedings <http://dx.doi.org/10.1038/npre.2012.7141.1> (Apr. 3, 2012).
Bogoch, et al., "Genomic Replikin Count Predicts Increased Lethality of Malaria," Nature Precedings <http://dx.doi.org/10.1038/npre.2012.7142.1> (Apr. 4, 2012).
Brenner, H., "Long-term survival rates of cancer patients achieved by the end of the 20th century: a period analysis," The Lancet, 360 (Oct. 12, 2002), pp. 1131-1135.
Ferro et al., "The androgen receptor CAG repeat: a modifier of carcinogenesis?" Molecular and Cellular Endocrinology, 193, Jan. 1, 2002, pp. 109-120.
Jackwood, M.W. "Efficacy of a Replikin Peptide Vaccine Against Low Pathogenicity Avian Influenza H5 Virus," Avian Diseases, Abstract, Pre-Print Jul. 4, 2009 at http://avdi.allenpress.com/avdionline/?request=get-abstract&doi=10.1637%2F8892-042509-ResNote.1.
Jackwood, M.W. "Efficacy of a replikin peptide vaccine against low-pathogenicity avian influenza H5 virus," Avian Dis. Dec. 2009;53(4):613-7.
Johansson et al., "Small, novel proteins from the mistletoe Pharadendron tementosum exhibit highly selective cytotoxicity to human breast cancer cells," Cell Mol. Life Sci, Jan. 2003, 60: 165-175.
Margalit et al., "Prediction of Immunodominant Helper T Cell Antigenic Sites From the Primary Sequence," Jour. of Immunology, vol. 138, 2213-2229, Apr. 1, 1987.
Melville et al., "P58IPK, a novel cochaperone containing tetratricopeptide repeats and a J-domain with oncogenic potential," Database accession No. PREV200000253165; & CMLS Cellular and Molecular Life Sciences, vol. 57, No. 2, Feb. 2000, pp. 311-322, ISSN: 1420-682X.
Niman et al., "Generation of protein-reactive antibodies by short peptides is an event of high frequency: Implications for the structural basis of immune recognition," PNAS USA 80:4949-4953 (1983).
Okuno et al., "A Common Neutralizing Epitope Conserved between the Hemagglutinins of Influenza A Virus H1 and H2 Strains," Journal of Virology, vol. 67, No. 5, May 1993, p. 2552-2558.
Simeckova-Rosenberg et al., "Protection of mice against lethal viral infection by synthetic peptides corresponding to B- and T-cell recognition sites of influenza A hemagglutinin," Vaccine, vol. 13, No. 10, pp. 927-932 (1995).
Smith et al., "Finding sequence motifs in groups of functionally related proteins," PNAS, vol. 87, pp. 826-830, Jan. 1990.
Takahashi et al., "Antibody to Ras proteins in patients with colon cancer," Clin Cancer Res, Oct. 1995, vol. 1, pp. 1071-1077.
Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.
Weber, E. et al., "Fine Mapping of a Peptide Sequence Containing an Antigenic Site Conserved Among Arenaviruses," Virology, vol. 164, p. 30-38 (1988).
Yao et al., "Linear epitopes of sperm whale myoglobin identified by polyclonal antibody screening of random peptide library," Int J Peptide Protein Res, Jun. 30, 1996, vol. 48, pp. 477-485.
Replikins, Ltd. Press Release, "Replikins, Ltd. has discovered a group of virus peptides that predict whether a virus is rapidly replicating and whether it is likely to spread" (Apr. 21, 2006).
Replikins, Ltd. Press Release, "Virus Replication Discovery Helps Predict Epidemics" (Apr. 24, 2006).
Replikins, Ltd. Press Release, "Flu forecaster firm born" (Apr. 28, 2006).
Boggs, J, Diagnostics & Imaging Week, "Replikins: Predicting global epidemics replication data" (May 4, 2006).
Replikins, Ltd. Press Release, "Replikins' FluForecast® Software Pinpoints Change in Deadly Bird Flu Amino Acid Sequence in Humans" (Jun. 2, 2006).
Replikins, Ltd. Press Release, "Advance Warning of H5N1 Influenza Outbreaks May Be Found in Shrimp Virus Reservoirs" (Oct. 25, 2006).
Replikins, Ltd. Press Release, "Rising H5N1 'Bird Flu' High-Virulence Sequences Found by Replikins, Ltd." (Nov. 6, 2006).
Replikins, Ltd. Press Release, "Human H5N1 Virus Replikin Count Overtakes Levels in H5N1 'Bird Flu'" (Dec. 27, 2006).
Replikins, Ltd. Press Release, "Gene Segment Identified in Virulent Human H5N1 Viruses—Key Discovery May Enable Development of Vaccines, Therapeutics" (Jan. 25, 2007).
Replikins, Ltd. Press Release, "High Host Mortality Rate Quantitatively Related to High Virus Replikin Count" (Mar. 6, 2007).
Replikins, Ltd. Press Release, "FluForecast® Trial in 2006 Predicted High Human H5N1 Mortality in Indonesia" (May 9, 2007).
Replikins, Ltd. Press Release, "Indonesia Reports Experiencing Human H5N1 Mortality Increase, as Predicted Last Year by Replikins' FluForecast® Quantitative Virus Analysis" (Jun. 8, 2007).
Replikins, LLC Press Release, "Replikins, LLC Finds West Nile Virus Replikin Count™ Has Reached Its Highest Recorded Value" (Aug. 3, 2007).
Replikins, LLC Press Release, "AMAS Test Measures Lethal Replikin Gene Activity in Lung and Other Cancers" (Dec. 6, 2007).
Replikins, Ltd. Press Release, "Lethal Human H5N1 Influenza Virus Replikin Gene Still Upregulated" (Dec. 11, 2007).

* cited by examiner

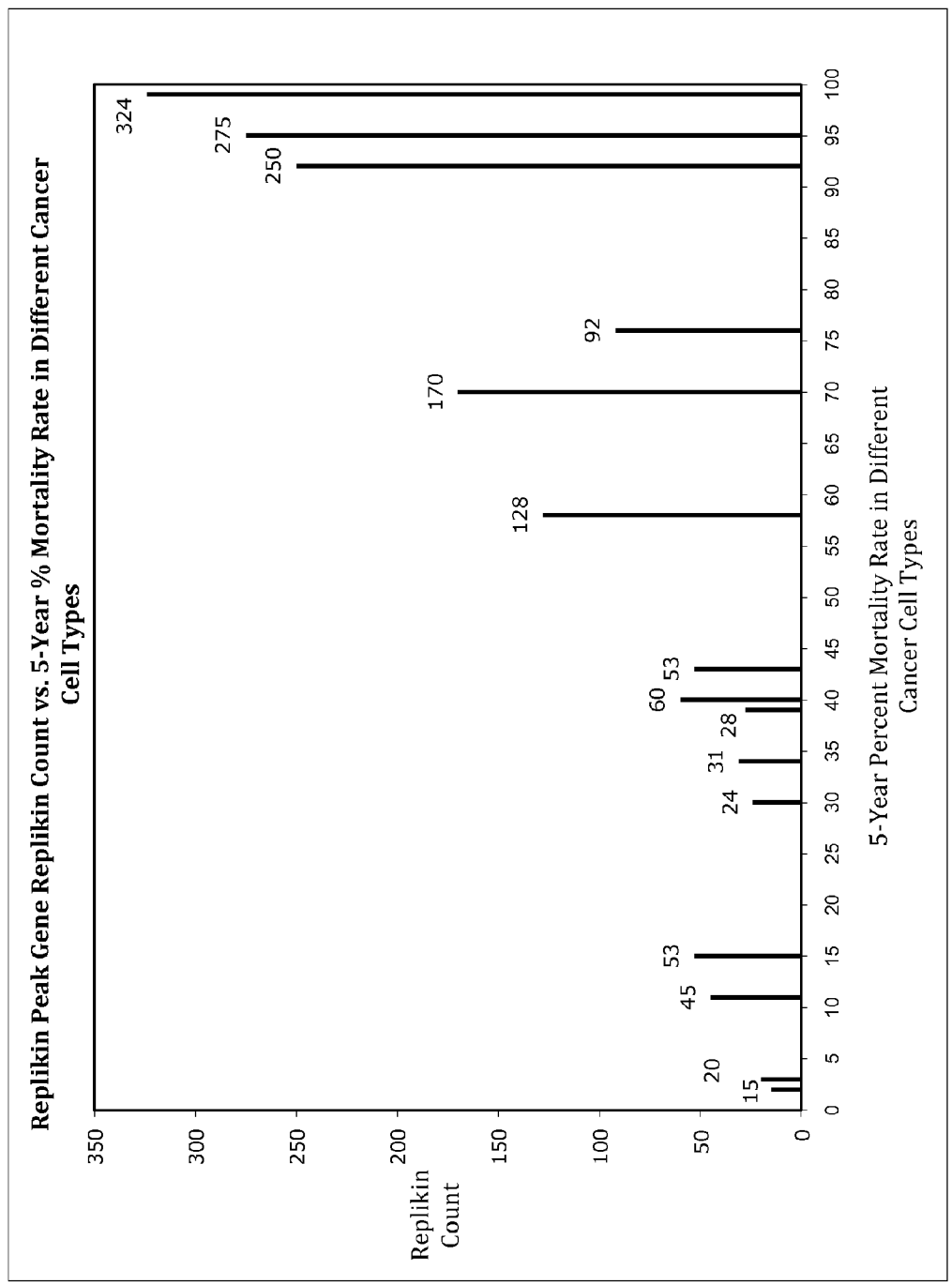

SEQUENCE LISTING

```
<160> NUMBER OF SEQ ID NOS: 203

<210> SEQ ID NO 1
<211> LENGTH: 7
<212> TYPE: PRT
<213> ORGANISM: Homo sapiens

<400> SEQUENCE: 1

Lys His Lys Asp Lys His Lys
1               5

<210> SEQ ID NO 2
<211> LENGTH: 8
<212> TYPE: PRT
<213> ORGANISM: Homo sapiens

<400> SEQUENCE: 2

His Lys His Lys Asp Lys His Lys
1               5

<210> SEQ ID NO 3
<211> LENGTH: 10
<212> TYPE: PRT
<213> ORGANISM: Homo sapiens

<400> SEQUENCE: 3

Lys His Lys Asp Arg Glu His Arg His Lys
1               5                   10

<210> SEQ ID NO 4
<211> LENGTH: 9
<212> TYPE: PRT
<213> ORGANISM: Homo sapiens

<400> SEQUENCE: 4

His Lys Asp Arg Glu His Arg His Lys
1               5
```

```
<210> SEQ ID NO 5
<211> LENGTH: 8
<212> TYPE: PRT
<213> ORGANISM: Homo sapiens

<400> SEQUENCE: 5

Lys Asp Arg Glu His Arg His Lys
1               5

<210> SEQ ID NO 6
<211> LENGTH: 8
<212> TYPE: PRT
<213> ORGANISM: Homo sapiens

<400> SEQUENCE: 6

His Lys Glu His Lys Lys Asp Lys
1               5

<210> SEQ ID NO 7
<211> LENGTH: 7
<212> TYPE: PRT
<213> ORGANISM: Homo sapiens

<400> SEQUENCE: 7

Lys Glu His Lys Lys Asp Lys
1               5

<210> SEQ ID NO 8
<211> LENGTH: 11
<212> TYPE: PRT
<213> ORGANISM: Homo sapiens

<400> SEQUENCE: 8

His Lys Lys Asp Lys Asp Lys Asp Arg Glu Lys
1               5                   10

<210> SEQ ID NO 9
<211> LENGTH: 13
<212> TYPE: PRT
<213> ORGANISM: Homo sapiens

<400> SEQUENCE: 9

Lys Lys Asp Lys Asp Lys Asp Arg Glu Lys Ser Lys His
1               5                   10

<210> SEQ ID NO 10
<211> LENGTH: 12
<212> TYPE: PRT
<213> ORGANISM: Homo sapiens

<400> SEQUENCE: 10

Lys Asp Lys Asp Lys Asp Arg Glu Lys Ser Lys His
1               5                   10

<210> SEQ ID NO 11
<211> LENGTH: 10
<212> TYPE: PRT
<213> ORGANISM: Homo sapiens

<400> SEQUENCE: 11

Lys Asp Lys Asp Arg Glu Lys Ser Lys His
1               5                   10
```

```
<210> SEQ ID NO 12
<211> LENGTH: 8
<212> TYPE: PRT
<213> ORGANISM: Homo sapiens

<400> SEQUENCE: 12

Lys Asp Arg Glu Lys Ser Lys His
1               5

<210> SEQ ID NO 13
<211> LENGTH: 10
<212> TYPE: PRT
<213> ORGANISM: Homo sapiens

<400> SEQUENCE: 13

Lys Ser Lys His Ser Asn Ser Glu His Lys
1               5                   10

<210> SEQ ID NO 14
<211> LENGTH: 13
<212> TYPE: PRT
<213> ORGANISM: Homo sapiens

<400> SEQUENCE: 14

His Lys Asp Lys His Lys Asp Arg Glu His Arg His Lys
1               5                   10

<210> SEQ ID NO 15
<211> LENGTH: 10
<212> TYPE: PRT
<213> ORGANISM: Homo sapiens

<400> SEQUENCE: 15

His Lys Met Phe Leu Met Leu Asp Asn Lys
1               5                   10

<210> SEQ ID NO 16
<211> LENGTH: 13
<212> TYPE: PRT
<213> ORGANISM: Homo sapiens

<400> SEQUENCE: 16

His Asn Val Lys Pro Glu Cys Leu Asp Ala Tyr Asn Lys
1               5                   10

<210> SEQ ID NO 17
<211> LENGTH: 13
<212> TYPE: PRT
<213> ORGANISM: Homo sapiens

<400> SEQUENCE: 17

His Asn Val Lys Pro Glu Cys Leu Glu Ala Tyr Asn Lys
1               5                   10

<210> SEQ ID NO 18
<211> LENGTH: 17
<212> TYPE: PRT
<213> ORGANISM: Homo sapiens

<400> SEQUENCE: 18

His Pro Gln Arg Pro Leu Val Leu Lys Thr Gly Val Gln Phe Thr Val
1               5                   10                  15

Lys
```

```
<210> SEQ ID NO 19
<211> LENGTH: 8
<212> TYPE: PRT
<213> ORGANISM: Homo sapiens

<400> SEQUENCE: 19

Lys Leu Gln Phe His Asn Val Lys
1               5

<210> SEQ ID NO 20
<211> LENGTH: 12
<212> TYPE: PRT
<213> ORGANISM: Homo sapiens

<400> SEQUENCE: 20

Lys Glu Thr Ser Ser Leu Tyr Lys Leu Gln Phe His
1               5                   10

<210> SEQ ID NO 21
<211> LENGTH: 15
<212> TYPE: PRT
<213> ORGANISM: Homo sapiens

<400> SEQUENCE: 21

His Ser Asn Leu Leu Ala Lys Lys Glu Thr Ser Ser Leu Tyr Lys
1               5                   10                  15

<210> SEQ ID NO 22
<211> LENGTH: 16
<212> TYPE: PRT
<213> ORGANISM: Homo sapiens

<400> SEQUENCE: 22

His Arg Ala Arg Glu Asp Ser Trp Leu Lys Ser Leu Phe Val Arg Lys
1               5                   10                  15

<210> SEQ ID NO 23
<211> LENGTH: 13
<212> TYPE: PRT
<213> ORGANISM: Homo sapiens

<400> SEQUENCE: 23

Lys Lys Glu Thr Ser Asn Leu Tyr Lys Leu Gln Phe His
1               5                   10

<210> SEQ ID NO 24
<211> LENGTH: 15
<212> TYPE: PRT
<213> ORGANISM: Homo sapiens

<400> SEQUENCE: 24

His Ser Asn Leu Leu Ala Lys Lys Glu Thr Ser Asn Leu Tyr Lys
1               5                   10                  15

<210> SEQ ID NO 25
<211> LENGTH: 15
<212> TYPE: PRT
<213> ORGANISM: Homo sapiens

<400> SEQUENCE: 25

Lys Ser Leu Phe Val Arg Lys Val Asp Pro Arg Lys Asp Ala His
1               5                   10                  15

<210> SEQ ID NO 26
<211> LENGTH: 10
```

```
<212> TYPE: PRT
<213> ORGANISM: Homo sapiens

<400> SEQUENCE: 26

Lys Asp Ala His Ser Asn Leu Leu Ala Lys
1               5                   10

<210> SEQ ID NO 27
<211> LENGTH: 22
<212> TYPE: PRT
<213> ORGANISM: Homo sapiens

<400> SEQUENCE: 27

Lys Asp Ala His Ser Asn Leu Leu Ala Lys Lys Glu Thr Ser Asn Leu
1               5                   10                  15

Tyr Lys Leu Gln Phe His
            20

<210> SEQ ID NO 28
<211> LENGTH: 16
<212> TYPE: PRT
<213> ORGANISM: Homo sapiens

<400> SEQUENCE: 28

Lys Ala Glu Cys Pro Leu Cys Lys Gln Pro Phe Asp Ser Ile Phe His
1               5                   10                  15

<210> SEQ ID NO 29
<211> LENGTH: 9
<212> TYPE: PRT
<213> ORGANISM: Homo sapiens

<400> SEQUENCE: 29

Lys Asp Glu Gln Ile Asn Lys Gly His
1               5

<210> SEQ ID NO 30
<211> LENGTH: 12
<212> TYPE: PRT
<213> ORGANISM: Homo sapiens

<400> SEQUENCE: 30

His Ser Val Leu Gly Lys Asp Glu Gln Ile Asn Lys
1               5                   10

<210> SEQ ID NO 31
<211> LENGTH: 9
<212> TYPE: PRT
<213> ORGANISM: Homo sapiens

<400> SEQUENCE: 31

Lys Asn His Arg Lys His His Gly Lys
1               5

<210> SEQ ID NO 32
<211> LENGTH: 9
<212> TYPE: PRT
<213> ORGANISM: Homo sapiens

<400> SEQUENCE: 32

Lys His His Gly Lys Lys Arg Met Lys
1               5

<210> SEQ ID NO 33
```

```
<211> LENGTH: 9
<212> TYPE: PRT
<213> ORGANISM: Homo sapiens

<400> SEQUENCE: 33

His Gly Lys Lys Arg Met Lys Ser Lys
1               5

<210> SEQ ID NO 34
<211> LENGTH: 9
<212> TYPE: PRT
<213> ORGANISM: Homo sapiens

<400> SEQUENCE: 34

Lys Lys Asn Asn His Ser Glu Arg Lys
1               5

<210> SEQ ID NO 35
<211> LENGTH: 8
<212> TYPE: PRT
<213> ORGANISM: Homo sapiens

<400> SEQUENCE: 35

Lys Asn Asn His Ser Glu Arg Lys
1               5

<210> SEQ ID NO 36
<211> LENGTH: 12
<212> TYPE: PRT
<213> ORGANISM: Homo sapiens

<400> SEQUENCE: 36

Lys Pro Gly Gly Lys Arg Lys Tyr Lys Thr Arg His
1               5                   10

<210> SEQ ID NO 37
<211> LENGTH: 9
<212> TYPE: PRT
<213> ORGANISM: Homo sapiens

<400> SEQUENCE: 37

Lys Ala Lys Asp Ser His Tyr Gln Lys
1               5

<210> SEQ ID NO 38
<211> LENGTH: 7
<212> TYPE: PRT
<213> ORGANISM: Homo sapiens

<400> SEQUENCE: 38

Lys Asp Ser His Tyr Gln Lys
1               5

<210> SEQ ID NO 39
<211> LENGTH: 8
<212> TYPE: PRT
<213> ORGANISM: Homo sapiens

<400> SEQUENCE: 39

Lys His Lys Arg Arg Lys Arg Lys
1               5

<210> SEQ ID NO 40
<211> LENGTH: 8
<212> TYPE: PRT
```

<213> ORGANISM: Homo sapiens

<400> SEQUENCE: 40

Lys Ala Thr Asp Thr Thr Lys His
1               5

<210> SEQ ID NO 41
<211> LENGTH: 7
<212> TYPE: PRT
<213> ORGANISM: Homo sapiens

<400> SEQUENCE: 41

Lys His His Lys Lys Lys Lys
1               5

<210> SEQ ID NO 42
<211> LENGTH: 10
<212> TYPE: PRT
<213> ORGANISM: Homo sapiens

<400> SEQUENCE: 42

His His Lys Lys Lys Lys Lys Lys His Lys
1               5                   10

<210> SEQ ID NO 43
<211> LENGTH: 9
<212> TYPE: PRT
<213> ORGANISM: Homo sapiens

<400> SEQUENCE: 43

His Lys Lys Lys Lys Lys Lys His Lys
1               5

<210> SEQ ID NO 44
<211> LENGTH: 8
<212> TYPE: PRT
<213> ORGANISM: Homo sapiens

<400> SEQUENCE: 44

Lys Lys Lys Lys Lys Lys His Lys
1               5

<210> SEQ ID NO 45
<211> LENGTH: 7
<212> TYPE: PRT
<213> ORGANISM: Homo sapiens

<400> SEQUENCE: 45

Lys Lys Lys Lys Lys His Lys
1               5

<210> SEQ ID NO 46
<211> LENGTH: 7
<212> TYPE: PRT
<213> ORGANISM: Homo sapiens

<400> SEQUENCE: 46

Lys Lys Lys Lys His Lys Lys
1               5

<210> SEQ ID NO 47
<211> LENGTH: 7
<212> TYPE: PRT
<213> ORGANISM: Homo sapiens

<400> SEQUENCE: 47

Lys Lys Lys His Lys Lys Lys
1               5

<210> SEQ ID NO 48
<211> LENGTH: 8
<212> TYPE: PRT
<213> ORGANISM: Homo sapiens

<400> SEQUENCE: 48

Lys Lys His Lys Lys Lys His Lys
1               5

<210> SEQ ID NO 49
<211> LENGTH: 6
<212> TYPE: PRT
<213> ORGANISM: Homo sapiens

<400> SEQUENCE: 49

Lys His Lys Lys His Lys
1               5

<210> SEQ ID NO 50
<211> LENGTH: 7
<212> TYPE: PRT
<213> ORGANISM: Homo sapiens

<400> SEQUENCE: 50

Lys His Lys Lys Lys His Lys
1               5

<210> SEQ ID NO 51
<211> LENGTH: 10
<212> TYPE: PRT
<213> ORGANISM: Homo sapiens

<400> SEQUENCE: 51

Lys His Lys Lys Lys His Lys Lys His His
1               5                   10

<210> SEQ ID NO 52
<211> LENGTH: 11
<212> TYPE: PRT
<213> ORGANISM: Homo sapiens

<400> SEQUENCE: 52

Lys Gly His Cys Asp Ser Ser Thr Arg Ile Lys
1               5                   10

<210> SEQ ID NO 53
<211> LENGTH: 7
<212> TYPE: PRT
<213> ORGANISM: Homo sapiens

<400> SEQUENCE: 53

Lys His Lys Asp Lys His Lys
1               5

<210> SEQ ID NO 54
<211> LENGTH: 8
<212> TYPE: PRT
<213> ORGANISM: Homo sapiens

<400> SEQUENCE: 54

His Lys His Lys Asp Lys His Lys
1               5

<210> SEQ ID NO 55
<211> LENGTH: 10
<212> TYPE: PRT
<213> ORGANISM: Homo sapiens

<400> SEQUENCE: 55

Lys His Lys Asp Arg Glu His Arg His Lys
1               5                   10

<210> SEQ ID NO 56
<211> LENGTH: 9
<212> TYPE: PRT
<213> ORGANISM: Homo sapiens

<400> SEQUENCE: 56

His Lys Asp Arg Glu His Arg His Lys
1               5

<210> SEQ ID NO 57
<211> LENGTH: 8
<212> TYPE: PRT
<213> ORGANISM: Homo sapiens

<400> SEQUENCE: 57

Lys Asp Arg Glu His Arg His Lys
1               5

<210> SEQ ID NO 58
<211> LENGTH: 8
<212> TYPE: PRT
<213> ORGANISM: Homo sapiens

<400> SEQUENCE: 58

His Lys Glu His Lys Lys Asp Lys
1               5

<210> SEQ ID NO 59
<211> LENGTH: 7
<212> TYPE: PRT
<213> ORGANISM: Homo sapiens

<400> SEQUENCE: 59

Lys Glu His Lys Lys Asp Lys
1               5

<210> SEQ ID NO 60
<211> LENGTH: 11
<212> TYPE: PRT
<213> ORGANISM: Homo sapiens

<400> SEQUENCE: 60

His Lys Lys Asp Lys Glu Lys Asp Arg Glu Lys
1               5                   10

<210> SEQ ID NO 61
<211> LENGTH: 13
<212> TYPE: PRT
<213> ORGANISM: Homo sapiens

<400> SEQUENCE: 61

Lys Lys Asp Lys Glu Lys Asp Arg Glu Lys Ser Lys His
1               5                   10

```
<210> SEQ ID NO 62
<211> LENGTH: 12
<212> TYPE: PRT
<213> ORGANISM: Homo sapiens

<400> SEQUENCE: 62

Lys Asp Lys Asp Lys Asp Arg Glu Lys Ser Lys His
1               5                   10

<210> SEQ ID NO 63
<211> LENGTH: 10
<212> TYPE: PRT
<213> ORGANISM: Homo sapiens

<400> SEQUENCE: 63

Lys Asp Lys Asp Arg Glu Lys Ser Lys His
1               5                   10

<210> SEQ ID NO 64
<211> LENGTH: 8
<212> TYPE: PRT
<213> ORGANISM: Homo sapiens

<400> SEQUENCE: 64

Lys Asp Arg Glu Lys Ser Lys His
1               5

<210> SEQ ID NO 65
<211> LENGTH: 10
<212> TYPE: PRT
<213> ORGANISM: Homo sapiens

<400> SEQUENCE: 65

Lys Ser Lys His Ser Asn Ser Glu His Lys
1               5                   10

<210> SEQ ID NO 66
<211> LENGTH: 13
<212> TYPE: PRT
<213> ORGANISM: Homo sapiens

<400> SEQUENCE: 66

His Lys Asp Lys His Lys Asp Arg Glu His Arg His Lys
1               5                   10

<210> SEQ ID NO 67
<211> LENGTH: 10
<212> TYPE: PRT
<213> ORGANISM: Homo sapiens

<400> SEQUENCE: 67

His Arg His Lys Glu His Lys Lys Asp Lys
1               5                   10

<210> SEQ ID NO 68
<211> LENGTH: 8
<212> TYPE: PRT
<213> ORGANISM: Homo sapiens

<400> SEQUENCE: 68

Lys Gly Lys Asp Tyr Ser Lys His
1               5
```

```
<210> SEQ ID NO 69
<211> LENGTH: 12
<212> TYPE: PRT
<213> ORGANISM: Homo sapiens

<400> SEQUENCE: 69

Lys Asp Lys Glu Lys Asp Arg Glu Lys Ser Lys His
1               5                   10

<210> SEQ ID NO 70
<211> LENGTH: 10
<212> TYPE: PRT
<213> ORGANISM: Homo sapiens

<400> SEQUENCE: 70

Lys Glu Lys Asp Arg Glu Lys Ser Lys His
1               5                   10

<210> SEQ ID NO 71
<211> LENGTH: 8
<212> TYPE: PRT
<213> ORGANISM: Homo sapiens

<400> SEQUENCE: 71

Lys His Ser Asn Ser Glu His Lys
1               5

<210> SEQ ID NO 72
<211> LENGTH: 14
<212> TYPE: PRT
<213> ORGANISM: Homo sapiens

<400> SEQUENCE: 72

His Ser Asn Ser Glu His Lys Asp Ser Glu Lys Lys His Lys
1               5                   10

<210> SEQ ID NO 73
<211> LENGTH: 9
<212> TYPE: PRT
<213> ORGANISM: Homo sapiens

<400> SEQUENCE: 73

His Lys Asp Ser Glu Lys Lys His Lys
1               5

<210> SEQ ID NO 74
<211> LENGTH: 8
<212> TYPE: PRT
<213> ORGANISM: Homo sapiens

<400> SEQUENCE: 74

Lys Asp Ser Glu Lys Lys His Lys
1               5

<210> SEQ ID NO 75
<211> LENGTH: 8
<212> TYPE: PRT
<213> ORGANISM: Homo sapiens

<400> SEQUENCE: 75

Lys Lys His Lys Glu Lys Glu Lys
1               5

<210> SEQ ID NO 76
<211> LENGTH: 10
```

-continued

<210> SEQ ID NO 76
<211> LENGTH: (not shown)
<212> TYPE: PRT
<213> ORGANISM: Homo sapiens

<400> SEQUENCE: 76

Lys Lys His Lys Glu Lys Glu Lys Thr Lys
1               5                   10

<210> SEQ ID NO 77
<211> LENGTH: 7
<212> TYPE: PRT
<213> ORGANISM: Homo sapiens

<400> SEQUENCE: 77

Lys His Lys Glu Lys Glu Lys
1               5

<210> SEQ ID NO 78
<211> LENGTH: 8
<212> TYPE: PRT
<213> ORGANISM: Homo sapiens

<400> SEQUENCE: 78

His Lys Glu Lys Glu Lys Thr Lys
1               5

<210> SEQ ID NO 79
<211> LENGTH: 8
<212> TYPE: PRT
<213> ORGANISM: Homo sapiens

<400> SEQUENCE: 79

Lys Glu Lys Glu Lys Thr Lys His
1               5

<210> SEQ ID NO 80
<211> LENGTH: 7
<212> TYPE: PRT
<213> ORGANISM: Homo sapiens

<400> SEQUENCE: 80

Lys Glu Lys Thr Lys His Lys
1               5

<210> SEQ ID NO 81
<211> LENGTH: 11
<212> TYPE: PRT
<213> ORGANISM: Homo sapiens

<400> SEQUENCE: 81

Lys Thr Lys His Lys Asp Gly Ser Ser Glu Lys
1               5                   10

<210> SEQ ID NO 82
<211> LENGTH: 9
<212> TYPE: PRT
<213> ORGANISM: Homo sapiens

<400> SEQUENCE: 82

Lys His Lys Asp Gly Ser Ser Glu Lys
1               5

<210> SEQ ID NO 83
<211> LENGTH: 8
<212> TYPE: PRT
<213> ORGANISM: Homo sapiens

<400> SEQUENCE: 83

His Lys Asp Gly Ser Ser Glu Lys
1               5

<210> SEQ ID NO 84
<211> LENGTH: 8
<212> TYPE: PRT
<213> ORGANISM: Homo sapiens

<400> SEQUENCE: 84

Lys Asp Gly Ser Ser Glu Lys His
1               5

<210> SEQ ID NO 85
<211> LENGTH: 10
<212> TYPE: PRT
<213> ORGANISM: Homo sapiens

<400> SEQUENCE: 85

His Lys Asp Lys His Lys Asp Arg Asp Lys
1               5                   10

<210> SEQ ID NO 86
<211> LENGTH: 9
<212> TYPE: PRT
<213> ORGANISM: Homo sapiens

<400> SEQUENCE: 86

Lys Asp Lys His Lys Asp Arg Asp Lys
1               5

<210> SEQ ID NO 87
<211> LENGTH: 7
<212> TYPE: PRT
<213> ORGANISM: Homo sapiens

<400> SEQUENCE: 87

Lys His Lys Asp Arg Asp Lys
1               5

<210> SEQ ID NO 88
<211> LENGTH: 9
<212> TYPE: PRT
<213> ORGANISM: Homo sapiens

<400> SEQUENCE: 88

His Lys Lys Glu Lys Asp Arg Glu Lys
1               5

<210> SEQ ID NO 89
<211> LENGTH: 11
<212> TYPE: PRT
<213> ORGANISM: Homo sapiens

<400> SEQUENCE: 89

Lys Glu His Lys Lys Glu Lys Asp Arg Glu Lys
1               5                   10

<210> SEQ ID NO 90
<211> LENGTH: 11
<212> TYPE: PRT
<213> ORGANISM: Homo sapiens

<400> SEQUENCE: 90

```
Lys Gly His Cys Asp Ser Ser Thr Arg Ile Lys
1               5                   10
```

<210> SEQ ID NO 91
<211> LENGTH: 8
<212> TYPE: PRT
<213> ORGANISM: Homo sapiens

<400> SEQUENCE: 91

```
His Lys Asp Arg Asp Lys Glu Lys
1               5
```

<210> SEQ ID NO 92
<211> LENGTH: 8
<212> TYPE: PRT
<213> ORGANISM: Homo sapiens

<400> SEQUENCE: 92

```
Lys Trp Lys Phe Leu Glu His Lys
1               5
```

<210> SEQ ID NO 93
<211> LENGTH: 10
<212> TYPE: PRT
<213> ORGANISM: Homo sapiens

<400> SEQUENCE: 93

```
Lys Met Leu Asp His Glu Tyr Thr Thr Lys
1               5                   10
```

<210> SEQ ID NO 94
<211> LENGTH: 10
<212> TYPE: PRT
<213> ORGANISM: Homo sapiens

<400> SEQUENCE: 94

```
Lys Val Pro Ser Pro Pro Pro Gly His Lys
1               5                   10
```

<210> SEQ ID NO 95
<211> LENGTH: 11
<212> TYPE: PRT
<213> ORGANISM: Homo sapiens

<400> SEQUENCE: 95

```
His Lys Trp Lys Glu Val Arg His Asp Asn Lys
1               5                   10
```

<210> SEQ ID NO 96
<211> LENGTH: 10
<212> TYPE: PRT
<213> ORGANISM: Homo sapiens

<400> SEQUENCE: 96

```
Lys Trp Lys Glu Val Arg His Asp Asn Lys
1               5                   10
```

<210> SEQ ID NO 97
<211> LENGTH: 8
<212> TYPE: PRT
<213> ORGANISM: Homo sapiens

<400> SEQUENCE: 97

```
Lys Glu Val Arg His Asp Asn Lys
```

```
<210> SEQ ID NO 98
<211> LENGTH: 9
<212> TYPE: PRT
<213> ORGANISM: Homo sapiens

<400> SEQUENCE: 98

His Lys Glu Arg Ile Ala Asn Phe Lys
1               5

<210> SEQ ID NO 99
<211> LENGTH: 8
<212> TYPE: PRT
<213> ORGANISM: Homo sapiens

<400> SEQUENCE: 99

Lys His Pro Thr Cys Pro Asn Lys
1               5

<210> SEQ ID NO 100
<211> LENGTH: 9
<212> TYPE: PRT
<213> ORGANISM: Homo sapiens

<400> SEQUENCE: 100

Lys Cys Asn Leu Gln Tyr His Phe Lys
1               5

<210> SEQ ID NO 101
<211> LENGTH: 10
<212> TYPE: PRT
<213> ORGANISM: Homo sapiens

<400> SEQUENCE: 101

Lys Lys Cys Asn Leu Gln Tyr His Phe Lys
1               5                   10

<210> SEQ ID NO 102
<211> LENGTH: 11
<212> TYPE: PRT
<213> ORGANISM: Homo sapiens

<400> SEQUENCE: 102

His Phe Pro Arg Lys Val Tyr Thr Cys Gly Lys
1               5                   10

<210> SEQ ID NO 103
<211> LENGTH: 12
<212> TYPE: PRT
<213> ORGANISM: Homo sapiens

<400> SEQUENCE: 103

His Asp Gln Lys Asn His Arg Lys His His Gly Lys
1               5                   10

<210> SEQ ID NO 104
<211> LENGTH: 7
<212> TYPE: PRT
<213> ORGANISM: Human immunodeficiency virus

<400> SEQUENCE: 104

Lys His Lys Asp Lys His Lys
1               5
```

```
<210> SEQ ID NO 105
<211> LENGTH: 8
<212> TYPE: PRT
<213> ORGANISM: Human immunodeficiency virus

<400> SEQUENCE: 105

His Lys His Lys Asp Lys His Lys
1               5

<210> SEQ ID NO 106
<211> LENGTH: 10
<212> TYPE: PRT
<213> ORGANISM: Human immunodeficiency virus

<400> SEQUENCE: 106

Lys His Lys Asp Arg Glu His Arg His Lys
1               5                   10

<210> SEQ ID NO 107
<211> LENGTH: 9
<212> TYPE: PRT
<213> ORGANISM: Human immunodeficiency virus

<400> SEQUENCE: 107

His Lys Asp Arg Glu His Arg His Lys
1               5

<210> SEQ ID NO 108
<211> LENGTH: 8
<212> TYPE: PRT
<213> ORGANISM: Human immunodeficiency virus

<400> SEQUENCE: 108

Lys Asp Arg Glu His Arg His Lys
1               5

<210> SEQ ID NO 109
<211> LENGTH: 8
<212> TYPE: PRT
<213> ORGANISM: Human immunodeficiency virus

<400> SEQUENCE: 109

His Lys Glu His Lys Lys Asp Lys
1               5

<210> SEQ ID NO 110
<211> LENGTH: 7
<212> TYPE: PRT
<213> ORGANISM: Human immunodeficiency virus

<400> SEQUENCE: 110

Lys Glu His Lys Lys Asp Lys
1               5

<210> SEQ ID NO 111
<211> LENGTH: 11
<212> TYPE: PRT
<213> ORGANISM: Human immunodeficiency virus

<400> SEQUENCE: 111

His Lys Lys Asp Lys Glu Lys Asp Arg Glu Lys
1               5                   10

<210> SEQ ID NO 112
```

```
<211> LENGTH: 13
<212> TYPE: PRT
<213> ORGANISM: Human immunodeficiency virus

<400> SEQUENCE: 112

Lys Lys Asp Lys Glu Lys Asp Arg Glu Lys Ser Lys His
1               5                   10

<210> SEQ ID NO 113
<211> LENGTH: 12
<212> TYPE: PRT
<213> ORGANISM: Human immunodeficiency virus

<400> SEQUENCE: 113

Lys Asp Lys Asp Lys Asp Arg Glu Lys Ser Lys His
1               5                   10

<210> SEQ ID NO 114
<211> LENGTH: 10
<212> TYPE: PRT
<213> ORGANISM: Human immunodeficiency virus

<400> SEQUENCE: 114

Lys Asp Lys Asp Arg Glu Lys Ser Lys His
1               5                   10

<210> SEQ ID NO 115
<211> LENGTH: 8
<212> TYPE: PRT
<213> ORGANISM: Human immunodeficiency virus

<400> SEQUENCE: 115

Lys Asp Arg Glu Lys Ser Lys His
1               5

<210> SEQ ID NO 116
<211> LENGTH: 13
<212> TYPE: PRT
<213> ORGANISM: Human immunodeficiency virus

<400> SEQUENCE: 116

His Lys Asp Lys His Lys Asp Arg Glu His Arg His Lys
1               5                   10

<210> SEQ ID NO 117
<211> LENGTH: 10
<212> TYPE: PRT
<213> ORGANISM: Human immunodeficiency virus

<400> SEQUENCE: 117

His Arg His Lys Glu His Lys Lys Asp Lys
1               5                   10

<210> SEQ ID NO 118
<211> LENGTH: 12
<212> TYPE: PRT
<213> ORGANISM: Human immunodeficiency virus

<400> SEQUENCE: 118

Lys Asp Lys Glu Lys Asp Arg Glu Lys Ser Lys His
1               5                   10

<210> SEQ ID NO 119
<211> LENGTH: 10
<212> TYPE: PRT
```

```
<213> ORGANISM: Human immunodeficiency virus

<400> SEQUENCE: 119

Lys Glu Lys Asp Arg Glu Lys Ser Lys His
1               5                   10

<210> SEQ ID NO 120
<211> LENGTH: 8
<212> TYPE: PRT
<213> ORGANISM: Human immunodeficiency virus

<400> SEQUENCE: 120

Lys His Ser Asn Ser Glu His Lys
1               5

<210> SEQ ID NO 121
<211> LENGTH: 14
<212> TYPE: PRT
<213> ORGANISM: Human immunodeficiency virus

<400> SEQUENCE: 121

His Ser Asn Ser Glu His Lys Asp Ser Glu Lys Lys His Lys
1               5                   10

<210> SEQ ID NO 122
<211> LENGTH: 9
<212> TYPE: PRT
<213> ORGANISM: Human immunodeficiency virus

<400> SEQUENCE: 122

His Lys Asp Ser Glu Lys Lys His Lys
1               5

<210> SEQ ID NO 123
<211> LENGTH: 8
<212> TYPE: PRT
<213> ORGANISM: Human immunodeficiency virus

<400> SEQUENCE: 123

Lys Asp Ser Glu Lys Lys His Lys
1               5

<210> SEQ ID NO 124
<211> LENGTH: 8
<212> TYPE: PRT
<213> ORGANISM: Human immunodeficiency virus

<400> SEQUENCE: 124

Lys Lys His Lys Glu Lys Glu Lys
1               5

<210> SEQ ID NO 125
<211> LENGTH: 7
<212> TYPE: PRT
<213> ORGANISM: Human immunodeficiency virus

<400> SEQUENCE: 125

Lys His Lys Glu Lys Glu Lys
1               5

<210> SEQ ID NO 126
<211> LENGTH: 8
<212> TYPE: PRT
<213> ORGANISM: Human immunodeficiency virus
```

```
<400> SEQUENCE: 126

His Lys Glu Lys Glu Lys Thr Lys
1               5

<210> SEQ ID NO 127
<211> LENGTH: 8
<212> TYPE: PRT
<213> ORGANISM: Human immunodeficiency virus

<400> SEQUENCE: 127

Lys Glu Lys Glu Lys Thr Lys His
1               5

<210> SEQ ID NO 128
<211> LENGTH: 7
<212> TYPE: PRT
<213> ORGANISM: Human immunodeficiency virus

<400> SEQUENCE: 128

Lys Glu Lys Thr Lys His Lys
1               5

<210> SEQ ID NO 129
<211> LENGTH: 11
<212> TYPE: PRT
<213> ORGANISM: Human immunodeficiency virus

<400> SEQUENCE: 129

Lys Thr Lys His Lys Asp Gly Ser Ser Glu Lys
1               5                   10

<210> SEQ ID NO 130
<211> LENGTH: 9
<212> TYPE: PRT
<213> ORGANISM: Human immunodeficiency virus

<400> SEQUENCE: 130

Lys His Lys Asp Gly Ser Ser Glu Lys
1               5

<210> SEQ ID NO 131
<211> LENGTH: 8
<212> TYPE: PRT
<213> ORGANISM: Human immunodeficiency virus

<400> SEQUENCE: 131

His Lys Asp Gly Ser Ser Glu Lys
1               5

<210> SEQ ID NO 132
<211> LENGTH: 8
<212> TYPE: PRT
<213> ORGANISM: Human immunodeficiency virus

<400> SEQUENCE: 132

Lys Asp Gly Ser Ser Glu Lys His
1               5

<210> SEQ ID NO 133
<211> LENGTH: 10
<212> TYPE: PRT
<213> ORGANISM: Human immunodeficiency virus

<400> SEQUENCE: 133
```

His Lys Asp Lys His Lys Asp Arg Asp Lys
1               5                   10

<210> SEQ ID NO 134
<211> LENGTH: 9
<212> TYPE: PRT
<213> ORGANISM: Human immunodeficiency virus

<400> SEQUENCE: 134

Lys Asp Lys His Lys Asp Arg Asp Lys
1               5

<210> SEQ ID NO 135
<211> LENGTH: 7
<212> TYPE: PRT
<213> ORGANISM: Human immunodeficiency virus

<400> SEQUENCE: 135

Lys His Lys Asp Arg Asp Lys
1               5

<210> SEQ ID NO 136
<211> LENGTH: 8
<212> TYPE: PRT
<213> ORGANISM: Human immunodeficiency virus

<400> SEQUENCE: 136

His Lys Asp Arg Asp Lys Glu Lys
1               5

<210> SEQ ID NO 137
<211> LENGTH: 7
<212> TYPE: PRT
<213> ORGANISM: Human immunodeficiency virus

<400> SEQUENCE: 137

Lys Glu His Lys Lys Glu Lys
1               5

<210> SEQ ID NO 138
<211> LENGTH: 9
<212> TYPE: PRT
<213> ORGANISM: Human immunodeficiency virus

<400> SEQUENCE: 138

Lys Glu His Lys His Lys Asp His Lys
1               5

<210> SEQ ID NO 139
<211> LENGTH: 8
<212> TYPE: PRT
<213> ORGANISM: Human immunodeficiency virus

<400> SEQUENCE: 139

Lys Trp Lys Phe Leu Glu His Lys
1               5

<210> SEQ ID NO 140
<211> LENGTH: 10
<212> TYPE: PRT
<213> ORGANISM: Human immunodeficiency virus

<400> SEQUENCE: 140

Lys Met Leu Asp His Glu Tyr Thr Thr Lys
1               5                   10

<210> SEQ ID NO 141
<211> LENGTH: 11
<212> TYPE: PRT
<213> ORGANISM: Human immunodeficiency virus

<400> SEQUENCE: 141

His Lys Trp Lys Glu Val Arg His Asp Asn Lys
1               5                   10

<210> SEQ ID NO 142
<211> LENGTH: 10
<212> TYPE: PRT
<213> ORGANISM: Human immunodeficiency virus

<400> SEQUENCE: 142

Lys Trp Lys Glu Val Arg His Asp Asn Lys
1               5                   10

<210> SEQ ID NO 143
<211> LENGTH: 8
<212> TYPE: PRT
<213> ORGANISM: Human immunodeficiency virus

<400> SEQUENCE: 143

Lys Glu Val Arg His Asp Asn Lys
1               5

<210> SEQ ID NO 144
<211> LENGTH: 11
<212> TYPE: PRT
<213> ORGANISM: Human immunodeficiency virus

<400> SEQUENCE: 144

Lys Gln Asn Gly Phe Ala Ser Pro His Ile Lys
1               5                   10

<210> SEQ ID NO 145
<211> LENGTH: 7
<212> TYPE: PRT
<213> ORGANISM: Human immunodeficiency virus

<400> SEQUENCE: 145

Lys His Arg Asp Lys Asp Lys
1               5

<210> SEQ ID NO 146
<211> LENGTH: 8
<212> TYPE: PRT
<213> ORGANISM: Human immunodeficiency virus

<400> SEQUENCE: 146

Lys Lys His Arg Asp Lys Asp Lys
1               5

<210> SEQ ID NO 147
<211> LENGTH: 8
<212> TYPE: PRT
<213> ORGANISM: Human immunodeficiency virus

<400> SEQUENCE: 147

Lys Asp Lys Glu His Lys His Lys
1               5

<210> SEQ ID NO 148
<211> LENGTH: 9
<212> TYPE: PRT
<213> ORGANISM: Human immunodeficiency virus

<400> SEQUENCE: 148

His Lys Lys Asp Lys Glu Arg Glu Lys
1               5

<210> SEQ ID NO 149
<211> LENGTH: 7
<212> TYPE: PRT
<213> ORGANISM: Homo sapiens

<400> SEQUENCE: 149

Lys His Lys Asp Lys His Lys
1               5

<210> SEQ ID NO 150
<211> LENGTH: 8
<212> TYPE: PRT
<213> ORGANISM: Homo sapiens

<400> SEQUENCE: 150

His Lys His Lys Asp Lys His Lys
1               5

<210> SEQ ID NO 151
<211> LENGTH: 10
<212> TYPE: PRT
<213> ORGANISM: Homo sapiens

<400> SEQUENCE: 151

Lys His Lys Asp Arg Glu His Arg His Lys
1               5                   10

<210> SEQ ID NO 152
<211> LENGTH: 9
<212> TYPE: PRT
<213> ORGANISM: Homo sapiens

<400> SEQUENCE: 152

His Lys Asp Arg Glu His Arg His Lys
1               5

<210> SEQ ID NO 153
<211> LENGTH: 8
<212> TYPE: PRT
<213> ORGANISM: Homo sapiens

<400> SEQUENCE: 153

Lys Asp Arg Glu His Arg His Lys
1               5

<210> SEQ ID NO 154
<211> LENGTH: 7
<212> TYPE: PRT
<213> ORGANISM: Homo sapiens

<400> SEQUENCE: 154

Lys Glu His Lys Lys Glu Lys
1               5

<210> SEQ ID NO 155
<211> LENGTH: 10

```
<212> TYPE: PRT
<213> ORGANISM: Homo sapiens

<400> SEQUENCE: 155

His Arg His Lys Glu His Lys Lys Glu Lys
1               5                   10

<210> SEQ ID NO 156
<211> LENGTH: 7
<212> TYPE: PRT
<213> ORGANISM: Homo sapiens

<400> SEQUENCE: 156

Lys His Lys Glu Lys Arg Lys
1               5

<210> SEQ ID NO 157
<211> LENGTH: 9
<212> TYPE: PRT
<213> ORGANISM: Homo sapiens

<400> SEQUENCE: 157

His Lys Lys Glu Lys Asp Arg Glu Lys
1               5

<210> SEQ ID NO 158
<211> LENGTH: 8
<212> TYPE: PRT
<213> ORGANISM: Homo sapiens

<400> SEQUENCE: 158

His Lys Glu His Lys Lys Glu Lys
1               5

<210> SEQ ID NO 159
<211> LENGTH: 9
<212> TYPE: PRT
<213> ORGANISM: Homo sapiens

<400> SEQUENCE: 159

Lys Glu His Lys His Lys Asp His Lys
1               5

<210> SEQ ID NO 160
<211> LENGTH: 8
<212> TYPE: PRT
<213> ORGANISM: Homo sapiens

<400> SEQUENCE: 160

Lys Trp Lys Phe Leu Glu His Lys
1               5

<210> SEQ ID NO 161
<211> LENGTH: 10
<212> TYPE: PRT
<213> ORGANISM: Homo sapiens

<400> SEQUENCE: 161

Lys Met Leu Asp His Glu Tyr Thr Thr Lys
1               5                   10

<210> SEQ ID NO 162
<211> LENGTH: 10
<212> TYPE: PRT
<213> ORGANISM: Homo sapiens
```

<400> SEQUENCE: 162

Lys Val Pro Ser Pro Pro Pro Gly His Lys
1               5                   10

<210> SEQ ID NO 163
<211> LENGTH: 11
<212> TYPE: PRT
<213> ORGANISM: Homo sapiens

<400> SEQUENCE: 163

His Lys Trp Lys Glu Val Arg His Asp Asn Lys
1               5                   10

<210> SEQ ID NO 164
<211> LENGTH: 10
<212> TYPE: PRT
<213> ORGANISM: Homo sapiens

<400> SEQUENCE: 164

Lys Trp Lys Glu Val Arg His Asp Asn Lys
1               5                   10

<210> SEQ ID NO 165
<211> LENGTH: 8
<212> TYPE: PRT
<213> ORGANISM: Homo sapiens

<400> SEQUENCE: 165

Lys Glu Val Arg His Asp Asn Lys
1               5

<210> SEQ ID NO 166
<211> LENGTH: 16
<212> TYPE: PRT
<213> ORGANISM: Homo sapiens

<400> SEQUENCE: 166

Lys Ala Glu Cys Pro Leu Cys Lys Gln Pro Phe Asp Ser Ile Phe His
1               5                   10                  15

<210> SEQ ID NO 167
<211> LENGTH: 9
<212> TYPE: PRT
<213> ORGANISM: Homo sapiens

<400> SEQUENCE: 167

Lys Asp Glu Gln Ile Asn Lys Gly His
1               5

<210> SEQ ID NO 168
<211> LENGTH: 12
<212> TYPE: PRT
<213> ORGANISM: Homo sapiens

<400> SEQUENCE: 168

His Ser Val Leu Gly Lys Asp Glu Gln Ile Asn Lys
1               5                   10

<210> SEQ ID NO 169
<211> LENGTH: 9
<212> TYPE: PRT
<213> ORGANISM: Homo sapiens

<400> SEQUENCE: 169

Lys Asn His Arg Lys His His Gly Lys
1               5

<210> SEQ ID NO 170
<211> LENGTH: 9
<212> TYPE: PRT
<213> ORGANISM: Homo sapiens

<400> SEQUENCE: 170

Lys His His Gly Lys Lys Arg Met Lys
1               5

<210> SEQ ID NO 171
<211> LENGTH: 9
<212> TYPE: PRT
<213> ORGANISM: Homo sapiens

<400> SEQUENCE: 171

His Gly Lys Lys Arg Met Lys Ser Lys
1               5

<210> SEQ ID NO 172
<211> LENGTH: 9
<212> TYPE: PRT
<213> ORGANISM: Homo sapiens

<400> SEQUENCE: 172

Lys Lys Asn Asn His Ser Glu Arg Lys
1               5

<210> SEQ ID NO 173
<211> LENGTH: 8
<212> TYPE: PRT
<213> ORGANISM: Homo sapiens

<400> SEQUENCE: 173

Lys Asn Asn His Ser Glu Arg Lys
1               5

<210> SEQ ID NO 174
<211> LENGTH: 12
<212> TYPE: PRT
<213> ORGANISM: Homo sapiens

<400> SEQUENCE: 174

Lys Pro Gly Gly Lys Arg Lys Tyr Lys Thr Arg His
1               5                   10

<210> SEQ ID NO 175
<211> LENGTH: 9
<212> TYPE: PRT
<213> ORGANISM: Homo sapiens

<400> SEQUENCE: 175

Lys Ala Lys Asp Ser His Tyr Gln Lys
1               5

<210> SEQ ID NO 176
<211> LENGTH: 7
<212> TYPE: PRT
<213> ORGANISM: Homo sapiens

<400> SEQUENCE: 176

Lys Asp Ser His Tyr Gln Lys

```
<210> SEQ ID NO 177
<211> LENGTH: 8
<212> TYPE: PRT
<213> ORGANISM: Homo sapiens

<400> SEQUENCE: 177

Lys His Lys Arg Arg Lys Arg Lys
1               5

<210> SEQ ID NO 178
<211> LENGTH: 8
<212> TYPE: PRT
<213> ORGANISM: Homo sapiens

<400> SEQUENCE: 178

Lys Ala Thr Asp Thr Thr Lys His
1               5

<210> SEQ ID NO 179
<211> LENGTH: 7
<212> TYPE: PRT
<213> ORGANISM: Homo sapiens

<400> SEQUENCE: 179

Lys His His Lys Lys Lys Lys
1               5

<210> SEQ ID NO 180
<211> LENGTH: 10
<212> TYPE: PRT
<213> ORGANISM: Homo sapiens

<400> SEQUENCE: 180

His His Lys Lys Lys Lys Lys Lys His Lys
1               5                   10

<210> SEQ ID NO 181
<211> LENGTH: 9
<212> TYPE: PRT
<213> ORGANISM: Homo sapiens

<400> SEQUENCE: 181

His Lys Lys Lys Lys Lys Lys His Lys
1               5

<210> SEQ ID NO 182
<211> LENGTH: 8
<212> TYPE: PRT
<213> ORGANISM: Homo sapiens

<400> SEQUENCE: 182

Lys Lys Lys Lys Lys Lys His Lys
1               5

<210> SEQ ID NO 183
<211> LENGTH: 7
<212> TYPE: PRT
<213> ORGANISM: Homo sapiens

<400> SEQUENCE: 183

Lys Lys Lys Lys Lys His Lys
1               5
```

<210> SEQ ID NO 184
<211> LENGTH: 7
<212> TYPE: PRT
<213> ORGANISM: Homo sapiens

<400> SEQUENCE: 184

Lys Lys Lys Lys His Lys Lys
1               5

<210> SEQ ID NO 185
<211> LENGTH: 7
<212> TYPE: PRT
<213> ORGANISM: Homo sapiens

<400> SEQUENCE: 185

Lys Lys Lys His Lys Lys Lys
1               5

<210> SEQ ID NO 186
<211> LENGTH: 8
<212> TYPE: PRT
<213> ORGANISM: Homo sapiens

<400> SEQUENCE: 186

Lys Lys His Lys Lys Lys His Lys
1               5

<210> SEQ ID NO 187
<211> LENGTH: 6
<212> TYPE: PRT
<213> ORGANISM: Homo sapiens

<400> SEQUENCE: 187

Lys His Lys Lys His Lys
1               5

<210> SEQ ID NO 188
<211> LENGTH: 7
<212> TYPE: PRT
<213> ORGANISM: Homo sapiens

<400> SEQUENCE: 188

Lys His Lys Lys Lys His Lys
1               5

<210> SEQ ID NO 189
<211> LENGTH: 10
<212> TYPE: PRT
<213> ORGANISM: Homo sapiens

<400> SEQUENCE: 189

Lys His Lys Lys Lys His Lys Lys His His
1               5                   10

<210> SEQ ID NO 190
<211> LENGTH: 11
<212> TYPE: PRT
<213> ORGANISM: Homo sapiens

<400> SEQUENCE: 190

Lys Gly His Cys Asp Ser Ser Thr Arg Ile Lys
1               5                   10

<210> SEQ ID NO 191

```
<211> LENGTH: 8
<212> TYPE: PRT
<213> ORGANISM: Homo sapiens

<400> SEQUENCE: 191

Lys Lys His Arg Asp Lys Asp Lys
1               5

<210> SEQ ID NO 192
<211> LENGTH: 8
<212> TYPE: PRT
<213> ORGANISM: Homo sapiens

<400> SEQUENCE: 192

His Lys Asp His Lys Lys Asp Lys
1               5

<210> SEQ ID NO 193
<211> LENGTH: 8
<212> TYPE: PRT
<213> ORGANISM: Homo sapiens

<400> SEQUENCE: 193

Lys Tyr Lys Asp Lys Glu His Lys
1               5

<210> SEQ ID NO 194
<211> LENGTH: 9
<212> TYPE: PRT
<213> ORGANISM: Homo sapiens

<400> SEQUENCE: 194

Lys Glu His Lys His Lys Asp His Lys
1               5

<210> SEQ ID NO 195
<211> LENGTH: 8
<212> TYPE: PRT
<213> ORGANISM: Homo sapiens

<400> SEQUENCE: 195

Lys Trp Lys Phe Leu Glu His Lys
1               5

<210> SEQ ID NO 196
<211> LENGTH: 10
<212> TYPE: PRT
<213> ORGANISM: Homo sapiens

<400> SEQUENCE: 196

Lys Met Leu Asp His Glu Tyr Thr Thr Lys
1               5                   10

<210> SEQ ID NO 197
<211> LENGTH: 10
<212> TYPE: PRT
<213> ORGANISM: Homo sapiens

<400> SEQUENCE: 197

Lys Val Pro Ser Pro Pro Gly His Lys
1               5                   10

<210> SEQ ID NO 198
<211> LENGTH: 11
<212> TYPE: PRT
```

```
<213> ORGANISM: Homo sapiens

<400> SEQUENCE: 198

His Lys Trp Lys Glu Val Arg His Asp Asn Lys
1               5                   10

<210> SEQ ID NO 199
<211> LENGTH: 10
<212> TYPE: PRT
<213> ORGANISM: Homo sapiens

<400> SEQUENCE: 199

Lys Trp Lys Glu Val Arg His Asp Asn Lys
1               5                   10

<210> SEQ ID NO 200
<211> LENGTH: 8
<212> TYPE: PRT
<213> ORGANISM: Homo sapiens

<400> SEQUENCE: 200

Lys Glu Val Arg His Asp Asn Lys
1               5

<210> SEQ ID NO 201
<211> LENGTH: 8
<212> TYPE: PRT
<213> ORGANISM: Homo sapiens

<400> SEQUENCE: 201

Lys Phe Tyr Tyr Asp Gly Lys His
1               5

<210> SEQ ID NO 202
<211> LENGTH: 10
<212> TYPE: PRT
<213> ORGANISM: Homo sapiens

<400> SEQUENCE: 202

His Ser Pro Lys Leu Glu Lys Ser Leu Lys
1               5                   10

<210> SEQ ID NO 203
<211> LENGTH: 7
<212> TYPE: PRT
<213> ORGANISM: Homo sapiens

<400> SEQUENCE: 203

Lys His Arg Asp Lys Asp Lys
1               5
```

US 9,320,784 B2

PEPTIDES SHARED AMONG LETHAL CANCERS AND THERAPEUTIC COMPOSITIONS COMPRISING SAID PEPTIDES

This application claims priority to U.S. Provisional Appln. Ser. No. 61/609,074, filed Mar. 9, 2012, U.S. Provisional Appln. Ser. No. 61/509,896, filed Jul. 20, 2011, U.S. application Ser. No. 12/581,112, filed Oct. 16, 2009, and U.S. application Ser. No. 12/538,027, filed Aug. 7, 2009.

This application incorporates the following by reference in their entireties: PCT/US09/61108, filed Oct. 16, 2009, PCT/US09/53208, filed Aug. 7, 2009, U.S. Provisional Appln. Ser. No. 61/246,006, filed Sep. 25, 2009, U.S. Provisional Appln. Ser. No. 61/185,160, filed Jun. 8, 2009, U.S. Provisional Appln. Ser. No. 61/179,686, filed May 19, 2009, U.S. application Ser. No. 12/429,044, filed Apr. 23, 2009, PCT/US2009/41565, filed Apr. 23, 2009, U.S. Provisional Appln. Ser. No. 61/172,115, filed Apr. 23, 2009, U.S. Provisional Appln. Ser. No. 61/143,618, filed Jan. 9, 2009, U.S. Provisional Appln. Ser. No. 61/087,354, filed Aug. 8, 2008, U.S. Provisional Appln. Ser. No. 61/054,010, filed May 16, 2008, U.S. application Ser. No. 12/108,458, filed Apr. 23, 2008, U.S. application Ser. No. 12/010,027, filed Jan. 18, 2008, U.S. Provisional Appln. Ser. No. 60/991,676, filed Nov. 30, 2007, U.S. application Ser. No. 11/923,559, filed Oct. 24, 2007, U.S. Provisional Appln. Ser. No. 60/982,336, filed Oct. 24, 2007, U.S. Provisional Appln. Ser. No. 60/982,333, filed Oct. 24, 2007, U.S. Provisional Appln. Ser. No. 60/982,338, filed Oct. 24, 2007, U.S. Provisional Appln. Ser. No. 60/935,816, filed Aug. 31, 2007, U.S. Provisional Appln. Ser. No. 60/935,499 filed Aug. 16, 2007, U.S. Provisional Appln. Ser. No. 60/954,743, filed Aug. 8, 2007, U.S. application Ser. No. 11/755,597, filed May 30, 2007, U.S. Provisional Appln. Ser. No. 60/898,097, filed Jan. 30, 2007, U.S. Provisional Appln. Ser. No. 60/880,966, filed Jan. 18, 2007, U.S. Provisional Appln. Ser. No. 60/853,744, filed Oct. 24, 2006, U.S. application Ser. No. 11/355,120, filed Feb. 16, 2006, now U.S. Pat. No. 7,894,999, U.S. application Ser. No. 11/116,203, filed Apr. 28, 2005, now U.S. Pat. No. 7,774,144, U.S. application Ser. No. 10/860,050, filed Jun. 4, 2004, now U.S. Pat. No. 7,442,761, U.S. application Ser. No. 10/189,437, filed Jul. 8, 2002, now U.S. Pat. No. 7,452,963, U.S. application Ser. No. 10/105,232, filed Mar. 26, 2002, now U.S. Pat. No. 7,189,800, U.S. application Ser. No. 09/984,057, filed Oct. 26, 2001, now U.S. Pat. No. 7,420,028, and U.S. application Ser. No. 09/984,056, filed Oct. 26, 2001, now U.S. Pat. No. 7,176,275.

SEQUENCE LISTING

The instant application contains a Sequence Listing, which has been submitted in ASCII format via EFS-Web and is hereby incorporated by reference in its entirety. Said ASCII copy, created on Nov. 30, 2012, is named 1379448102.txt and is 31,008 bytes in size.

TECHNICAL FIELD OF THE INVENTION

This invention relates generally to peptides identified as conserved across different types of cancer. The invention is further directed to diagnosis, prevention and treatment of cancer within and across cancer types.

BACKGROUND OF THE INVENTION

Cancer is a class of diseases in which cells divide absent limits that normally control growth of cells in tissue. Uncontrolled cancer cell growth often leads to invasion and destruction of tissues adjacent to the cancer cells since cancer cells are typically capable of living in environments different from the tissue from which the cells were transformed. As a result, cancer cells often spread to other locations in the body where they may rapidly replicate causing additional tumors, resulting trauma, and sometimes death. The rate at which a line of cancer cells replicates is often a determining factor in the aggressiveness and eventual lethality of the cancer. Rates of replication for particular types of cancer are also considered in developing strategies for cancer therapy.

Nearly all cancer cells are abnormal in their genetic material as compared to cells from which they were transformed. Some progress has been made in developing therapies that more directly target the molecular abnormalities in cancer cells. These therapies ideally inhibit or kill cancer cells while not extensively damaging normal cells. Nevertheless, the progress that has been made in developing targeted therapies remains severely insufficient since about one-quarter of deaths in the United States in 2011 are expected to have resulted from cancer.

Development of therapies that more directly target the molecular abnormalities in cancer cells has traditionally been directed to identifying specific abnormalities shared by one histological cancer type or by related cancer types. Such therapies have generally not been directed to abnormalities shared across cancer types. As such, therapies that more directly target molecular abnormalities have been generally limited to narrow categories of patients suffering from cancer of a specific histological type with a specifically-identified molecular abnormality.

Replikin peptides are a family of small peptides that have been correlated with the phenomenon of rapid replication in malignancies, as well as viruses, and other infectious organisms, and have been noted to be conserved in pathogens. The association of Replikin peptides with rapid replication has been described in U.S. Pat. Nos. 7,189,800, 7,894,999, and 7,442,761, among others. Both Replikin concentration (number of Replikins per 100 amino acids) and Replikin composition have been correlated with the functional phenomenon of rapid replication.

Replikin peptides have likewise been identified as candidates for vaccine development in viruses and other pathogens including as candidates for vaccines across strains of pathogen, such as across strains of influenza. See, e.g., U.S. application Ser. No. 12/581,112. Immunogenic and/or protective trials using Replikin-based vaccines have demonstrated success in influenza virus, taura syndrome virus, and SARS coronavirus as well as glioblastoma, small cell lung, and lymphoma cancers. See, e.g., U.S. application Ser. No. 12/581,112, U.S. application Ser. No. 12/108,458, U.S. Pat. No. 7,442,761, and U.S. Pat. No. 7,420,028 (FIG. 4). Nevertheless, Replikin peptides have not previously been identified as expressly conserved across types of cancer and no therapies have until now been developed using such conserved peptides across different types of cancer. Identification of such peptides would provide the medical community with therapies useful across cancer types where the therapies would be directed at peptides involved in rapid replication in malignancy. Such therapies would additionally provide more flexible treatments for cancer and would reduce productions costs, distribution costs, diagnostic costs, therapeutic costs and storage costs.

Need remains in the art for identification of peptides useful in vaccines against cancer. Need likewise remains in the art for therapies directed against molecular abnormalities that are shared across cancer types.

SUMMARY OF THE INVENTION

The present invention provides compositions for interfering with replication in cancer, isolated or synthesized peptides in various types of cancer, including peptides that are shared among various types of cancer and peptides, polypeptides, and protein fragments comprising said peptides. Sharing of these peptides among cancer types and among cancer types and virus types is an unexpected finding. The invention also provides immunogenic compositions, therapeutic agents, diagnostic agents, and vaccines comprising said isolated or synthesized peptides or comprising proteins, protein fragments, polypeptides, or other compounds comprising said peptides. The invention also provides antibodies, antibody fragments, and other binding agents, as well as antisense nucleic acids and siRNAs directed against expression of peptides shared among the various types of cancer, as well as proteins, protein fragments, polypeptides, or other compounds comprising said peptides.

A first non-limiting aspect of the invention provides a composition for interfering with replication of cancer. In a non-limiting embodiment, the composition may comprise at least one sequence of SEQ ID NO(s): 1-203, at least one peptide consisting essentially of at least one of SEQ ID NO(s): 1-203, at least one peptide consisting of at least one of SEQ ID NO(s): 1-203, at least one protein comprising at least one of SEQ ID NO(s): 1-203, at least one protein fragment comprising at least one of SEQ ID NO(s): 1-203, at least one polypeptide comprising at least one of SEQ ID NO(s): 1-203, or at least one peptide comprising at least one of SEQ ID NO(s): 1-203. In a further non-limiting embodiment, the composition may comprise a mixture of at least two peptides of SEQ ID NO(s): 1-27, SEQ ID NO(s): 28-52, SEQ ID NO(s): 53-103, SEQ ID NO(s): 104-148, SEQ ID NO(s): 149-165, and SEQ ID NO(s): 166-203. In another non-limiting embodiment, the composition is capable of interfering with cancer indirectly through the immune system. In another non-limiting embodiment, the composition is capable of interfering with cancer through direct interference. In another non-limiting embodiment, the composition comprises at least one functional fragment of at least one of SEQ ID NO(s): 1-203. A composition for interfering with replication in cancer may be directed against endodermic, ectodermic, and mesodermic cancer types as well as cancers arising from HIV.

A second non-limiting aspect of the invention provides an isolated or synthesized protein fragment or peptide comprising at least one of SEQ ID NO(s): 1-203 or a sequence sharing at least 70% identity with at least one of SEQ ID NO(s): 1-203. The isolated or synthesized protein fragment or peptide may consist essentially of a peptide of at least one of SEQ ID NO(s): 1-203 or may consist of at least one of SEQ ID NO(s): 1-203. Another non-limiting embodiment of the second aspect of the invention provides an isolated or synthesized protein fragment or peptide comprising a functional fragment of at least one of SEQ ID NO(s): 1-203, A third non-limiting aspect of the invention provides a vaccine comprising at least one of SEQ ID NO(s): 1-27, SEQ ID NO(s): 28-52, SEQ ID NO(s): 53-103, SEQ ID NO(s): 104-148, SEQ ID NO(s): 149-165, and SEQ ID NO(s): 166-203 or a sequence sharing at least 70% identity with at least one of SEQ ID NO(s): 1-27, SEQ ID NO(s): 28-52, SEQ ID NO(s): 53-103, SEQ ID NO(s): 104-148, SEQ ID NO(s): 149-165, and SEQ ID NO(s): 166-203. In a non-limiting embodiment, the vaccine comprises a functional fragment of at least one of SEQ ID NO(s): 1-27, SEQ ID NO(s): 28-52, SEQ ID NO(s): 53-103, SEQ ID NO(s): 104-148, SEQ ID NO(s): 149-165, and SEQ ID NO(s): 166-203. In a non-limiting embodiment, the vaccine may comprise a mixture of at least two of a sequence of SEQ ID NO(s): 1-203 or a sequence sharing at least 70% identity with a sequence of SEQ ID NO(s): 1-203. In another non-limiting embodiment, the vaccine may comprise a functional fragment of a sequence of SEQ ID NO(s): 1-203. The vaccine may be directed against cancer in a patient suffering from HIV comprising at least one sequence of SEQ ID NO(s): 104-148 or a sequence sharing at least 70% identity with a sequence of SEQ ID NO(s): 104-148. The vaccine may also be directed against glioblastoma multiforme, pancreatic cancer, lung cancer, leukemia, colon cancer, colorectal cancer, cervical cancer, and/or breast cancer.

In a non-limiting embodiment of the third aspect of the invention, the vaccine is directed at least against glioblastoma multiforme cancer and comprises a sequence of SEQ ID NO(s): 1-27 or a sequence sharing at least 70% identity with a sequence of SEQ ID NO(s): 1-27. In another non-limiting embodiment, the vaccine is directed at least against pancreatic cancer and comprises a sequence of SEQ ID NO(s): 28-52 or a sequence sharing at least 70% identity with a sequence of SEQ ID NO(s): 28-52. In another non-limiting embodiment, the vaccine is directed at least against lung cancer comprising a sequence of SEQ ID NO(s): 53-103 or a sequence sharing at least 70% identity with a sequence of SEQ ID NO(s): 53-103. In another non-limiting embodiment, the vaccine is directed at least against leukemia and comprises a sequence of SEQ ID NO(s): 149-165 or a sequence sharing at least 70% identity with a sequence of SEQ ID NO(s): 149-165. In another non-limiting embodiment, the vaccine is directed at least against colon cancer, colorectal cancer, or cervical cancer comprising a sequence of SEQ ID NO(s): 166-193 or a sequence sharing at least 70% identity with a sequence of SEQ ID NO(s): 166-193. In another non-limiting embodiment, the vaccine is directed at least against breast cancer comprising a sequence of SEQ ID NO(s): 194-203 or a sequence sharing at least 70% identity with a sequence of SEQ ID NO(s): 194-203. In a further non-limiting embodiment, a vaccine comprises at least one protein comprising at least one of SEQ ID NO(s): 1-203 or at least one protein fragment comprising at least one of SEQ ID NO(s): 1-203. In a further non-limiting embodiment, the vaccine is directed against glioblastoma multiforme, lung cancer, and leukemia. In a further non-limiting embodiment, the vaccine is directed against pancreatic cancer and colon cancer, colorectal cancer, and/or cervical cancer. In a further non-limiting embodiment, the vaccine is directed against lung cancer, leukemia, and breast cancer.

A fourth non-limiting aspect of the invention provides an isolated, chemically-synthesized, or recombinantly-generated binding molecule that specifically binds at least one sequence of SEQ ID NO(s): 1-203. In a non-limiting embodiment, the isolated, chemically-synthesized, or recombinantly-generated binding molecule is an antibody or an antibody fragment. In a non-limiting embodiment, the binding molecule specifically binds at least one functional fragment of SEQ ID NO(s): 1-203. In a further non-limiting embodiment, the binding molecule may be administered to an animal or human to provide passive immunity.

A fifth non-limiting aspect of the invention provides isolated or synthesized peptides or polypeptides comprising at least one of the peptides of SEQ ID NO(s): 1-203. In an embodiment of the fifth aspect of the present invention, the isolated or synthesized peptides or polypeptides comprising at least one of SEQ ID NO(s): 1-203 are comprised within a protein, protein fragment, or polypeptide. In a further embodiment, an immunogenic portion of the protein, protein fragment, or polypeptide is a peptide of SEQ ID NO(s): 1-203. In a further embodiment, the protein, protein fragment, or polypeptide comprises up to 200 additional amino acid residues on the C-terminus of the at least one peptide of SEQ ID NO(s): 1-203 and/or up to 200 additional amino acid residues on the N-terminus of the at least one peptide of SEQ ID NO(s): 1-203. In a further embodiment, the protein, protein fragment, or polypeptide comprises up to 100 additional amino acid residues on the C-terminus and/or up to 100 additional amino acid residues on the N-terminus of the at least one peptide of SEQ ID NO(s): 1-203. In a further embodiment the C-terminus has up to 50 additional amino acid residues and/or the N-terminus has up to 50 additional amino acid residues. In yet a further embodiment, the C-terminus has up to 5, 10, or 25 additional amino acid residues and/or the N-terminus has up to 1, 2, 3, 4, 5, 10, or 25 additional amino acid residues. In a further embodiment, at least one peptide of SEQ ID NO(s): 1-203 is the immunogenic or otherwise active portion of the protein, protein fragment, or polypeptide.

In another embodiment of the fifth aspect of the invention, the isolated or synthesized peptide consists essentially of at least one of SEQ ID NO(s): 1-203. In yet a further embodiment, the isolated or synthesized peptide consists of at least one of SEQ ID NO(s): 1-203.

Another non-limiting embodiment of the fifth aspect of the invention provides a protein fragment, polypeptide, or other compound comprising a functional fragment of at least one of SEQ ID NO(s): 1-203. Yet another non-limiting embodiment provides a peptide consisting essentially of a functional fragment of at least one of SEQ ID NO(s): 1-203 or a peptide consisting of at least one of SEQ ID NO(s): 1-203.

A sixth aspect of the present invention provides an immunogenic composition comprising at least one of the peptides of SEQ ID NO(s): 1-203. One embodiment of the sixth aspect of the invention is composition comprising a protein, protein fragment, polypeptide or other compound comprising at least one of the sequences of SEQ ID NO(s): 1-203. Another non-limiting embodiment is a composition comprising a protein, protein fragment, polypeptide or other compound consisting essentially of at least one of the sequences of SEQ ID NO(s): 1-203. Another non-limiting embodiment is a composition comprising a peptide consisting of at least one of the sequences of SEQ ID NO(s): 1-203. Another non-limiting embodiment is a composition comprising a protein, protein fragment, polypeptide, or other compound comprising, consisting essentially of, or consisting of a functional fragment of at least one of the peptides of SEQ ID NO(s): 1-203.

A seventh aspect of the invention provides a vaccine against cancer. In an embodiment of the seventh aspect of the invention, the vaccine comprises at least one peptide of SEQ ID NO(s): 1-203. In a further non-limiting embodiment, the vaccine comprises at least two, at least three, at least four, or more peptides of SEQ ID NO(s): 1-203. In a non-limiting embodiment, the vaccine may comprise at least one functional fragment of at least one peptide of SEQ ID NO(s): 1-203. The vaccine may comprise a pharmaceutically acceptable carrier and/or adjuvant. In a further non-limiting embodiment, the vaccine is directed against any histological type of cancer. In another non-limiting embodiment, the vaccine is directed against glioblastoma multiforme, pancreatic cancer, lung cancer, leukemia, colon cancer, colorectal cancer, cervical cancer, breast cancer, and/or cancer arising in association with a viral infection, including a viral infection of HIV. In a further non-limiting embodiment, the vaccine comprises at least one of SEQ ID NO(s): 1-27, 53-103, 104-148, 149-165, or 194-203 and is directed against glioblastoma multiforme, lung cancer, leukemia, or breast cancer. In a further embodiment, the vaccine comprises a mixture of at least one of SEQ ID NO(s): 1-27, at least one of SEQ ID NO(s): 53-103, at least one of SEQ ID NO(s): 149-165, and at least one of SEQ ID NO(s): 194-203. In a further non-limiting embodiment, the vaccine also comprises at least one of SEQ ID NO(s): 104-148. In another non-limiting embodiment, the vaccine comprises at least one SEQ ID NO(s): 1-14, 53-66, 104-116, 149-154, or 157-165 or a mixture of two or more of SEQ ID NO(s): 1-14, 53-66, 104-116, 149-154, or 157-165.

In a further non-limiting embodiment, the vaccine comprises a mixture of at least one of SEQ ID NO(s): 28-52 and 166-190 and is directed against pancreatic cancer, colon cancer, colorectal cancer, or cervical cancer. In a further non-limiting embodiment, the vaccine comprises a mixture of at least one of SEQ ID NO(s): 28-52 and at least one of SEQ ID NO(s): 166-190. In a further embodiment, the vaccine comprises a mixture of at least one of SEQ ID NO(s): 28-43 and 48-52 and at least one of SEQ ID NO(s): 166-181 and 186-190.

An eighth aspect of the present invention provides use of a protein, protein fragment, or polypeptide comprising at least one of SEQ ID NO(s): 1-203, a peptide consisting essentially of at least one of SEQ ID NO(s): 1-203, or a peptide consisting of at least one of SEQ ID NO(s): 1-203 for administration to an animal to provide an immune response and/or to provide a protective effect against cancer. An embodiment of the eighth aspect of the present invention provides a method of stimulating the immune system.

BRIEF DESCRIPTION OF THE DRAWINGS

FIG. 1 illustrates a quantitative relationship between the concentration of Replikin peptides in the Replikin Peak Gene of individual proteins associated with cancer cells of a plurality of common human malignancies and five-year percent mortality rates for each of the plurality of common human malignancies. Replikin Count was determined from the highest Replikin Count identified in a Replikin Peak Gene of sequences surveyed at www.pubmed.com and is reflected on the X-axis of the graph of FIG. 1 as the highest Replikin Count of the Replikin Peak Gene of a protein associated with a given cancer-cell type. The five-year percent mortality rates are reflected on the Y-axis of the graph of FIG. 1. The data are as reported in Brenner, H., "Long-term survival rates of cancer patients achieved by the end of the 20th century: a period analysis," The Lancet, 360 (Oct. 12, 2002), 1131-1135. Within FIG. 1, the bar labeled "15" reflects the Replikin Count observed in cancers of the thyroid, the bar labeled "20" reflects the Replikin Count observed in cancers of the prostate, the bar labeled "45" reflects the Replikin Count observed in cancers of the breast, the bar labeled "53" above the 15% mortality rate on the X-axis of the FIGURE reflects the mean Replikin Count observed in urinary bladder cancer, the bar labeled "24" reflects the mean Replikin Count observed in cancers of the uterin corpus, the bar labeled "31" reflects the mean Replikin Count observed in cancers of the uterin cervix, the bar labeled "28" reflects the mean Replikin Count observed in cancers of the colon, the bar labeled "60" reflects the mean Replikin Count observed in cancers of the ovary, the bar labeled "53" above the 43% mortality rate on the X-axis of the FIGURE reflects the mean Replikin Count observed in cancers of the oral cavity, the bar labeled "128" reflects the mean Replikin Count observed in lymphocytic leukemia, the bar labeled "170" reflects the mean Replikin Count observed in multiple myelomas, the bar labeled "92" reflects the mean Replikin Count observed in gastric cancers, the bar labeled "250" reflects the mean Replikin Count observed in non-small cell carcinomas of the lung, the bar labeled "275" reflects the mean Replikin Count observed in cancers of the pancreas, and the bar labeled "324" reflects the mean Replikin Count observed in glioblastoma cancers. The lowest Replikin concentrations are seen in thyroid cancer (15 Replikin sequences per 100 amino acids) and in prostate cancer (20 Replikin sequences per 100 amino acids) and the lowest five-year mortality rates are seen in thyroid cancer (2%) and prostate cancer (3%). The highest Replikin concentrations are seen in non-small cell lung carcinoma (250 Replikin sequences per 100 amino acids), in pancreatic cancer (275 Replikin sequences per 100 amino acids), and in glioblastoma (324 Replikin sequences per 100 amino acids) and the highest five-year mortality rates are seen in non-small cell lung carcinoma (92%), pancreatic cancer (95%), and glioblastoma (99%). These data illustrate a relationship between Replikin concentration in a given type of cancer and lethality in that type of cancer as compared to the Replikin concentration and lethality in other types of cancer.

DETAILED DESCRIPTION OF THE INVENTION

Definitions

As used herein, a "Replikin sequence" is an amino acid sequence of 7 to 50 amino acids having at least one lysine residue on one end of the sequence and at least one lysine residue or at least one histidine residue located on the other end of the sequence and comprising
  (1) a first lysine residue located six to ten residues from a second lysine residue;
  (2) at least one histidine residue; and
  (3) at least 6% lysine residues.
This definition is a strict definition for purposes of counting Replikin sequences and for purposes of identifying Replikin sequences. For diagnostic, therapeutic, and preventive purposes, a Replikin sequence may be an amino acid sequence of 7 to about 50 amino acid residues with (1) a first lysine residue located six to ten residues from a second lysine residue; (2) at least one histidine residue; and (3) at least 6% lysine residues. For diagnostic, therapeutic, and preventive purposes, the definition of a Replikin sequence provides for the function of Replikin sequences, namely, the function of rapid replication in an organism and the function of immunogenicity when introduced to an immune system. Each of the sequences listed in Table 1 is a Replikin sequence by the above strict definition.

The term "Replikin sequence" can also refer to a nucleic acid sequence encoding an amino acid sequence having 7 to about 50 amino acids comprising:
  (1) at least one lysine residue located six to ten amino acid residues from a second lysine residue;
  (2) at least one histidine residue; and
  (3) at least 6% lysine residues,
wherein the amino acid sequence may comprise a terminal lysine and may further comprise a terminal lysine or a terminal histidine.

As used herein, "interfering with replication in cancer" means capable of altering replication rate of cancer cells when administered to an animal or human suffering from a cancer. A composition may interfere with replication in cancer directly or indirectly, such as through an immune response. Replikin sequences have been demonstrated to interfere with replication in, for example, viruses such a taura syndrome virus and Low-Pathogenic H5N1. See, e.g., U.S. application Ser. No. 12/108,458 and U.S. application Ser. No. 12/581,112. In taura syndrome virus in shrimp, the interaction between Replikin sequences and rapid replication of the virus is understood to be direct, at least in part, since shrimp are not known to have an immune system that produces antibodies or analogous binding molecules. See, e.g., U.S. application Ser. No. 12/108,458.

As used herein, the term "peptide" refers to a compound of two or more amino acids in which the carboxyl group of one amino acid is attached to an amino group of another amino acid via a peptide bond. As used herein, "isolated" or "synthesized" peptide or protein or biologically active portion of a peptide or protein refers to a peptide that is, after purification, substantially free of cellular material or other contaminating proteins or peptides from the cell or tissue source from which the peptide is derived, or substantially free from chemical precursors or other chemicals when chemically synthesized by any method, or substantially free from contaminating peptides when synthesized by recombinant gene techniques. A protein or peptide may be isolated in silico from nucleic acid or amino acid sequences that are available through public or private databases or sequence collections and then may be synthesized through chemical or recombinant means. An "encoded" or "expressed" protein, protein sequence, protein fragment sequence, or peptide sequence is a sequence encoded by a nucleic acid sequence that encodes the amino acids of the protein or peptide sequence with any codon known to one of ordinary skill in the art now or hereafter. It should be noted that it is well known in the art that, due to redundancy in the genetic code, individual nucleotides can be readily exchanged in a codon and still result in an identical amino acid sequence. As will be understood by one of skill in the art, a method of identifying a Replikin amino acid sequence also encompasses a method of identifying a nucleic acid sequence that encodes a Replikin amino acid sequence wherein the Replikin amino acid sequence is encoded by the identified nucleic acid sequence.

As used herein, a "protein fragment" is any portion of an expressed whole protein. A protein fragment may reflect an expressed whole protein with one or more amino acids removed from the amino acid sequence of the expressed whole protein. A whole protein or expressed whole protein may reflect a whole protein or expressed whole protein that has been subject to cellular processing to create a protein that is capable of functioning in a replication system in a proper manner. A protein fragment may reflect an amino acid sequence that is at least 30%, 40%, 50%, 60%, 70%, 80%, 90%, 95%, or 100% homologous with any portion of an expressed whole protein, said portion being less than the entirety of the expressed whole protein. A "polypeptide," as used in this specification, is any portion of a protein fragment and is less than an expressed whole protein. A peptide is less than a protein, protein fragment, or polypeptide. With respect to the sequences disclosed in Table 1, the ordinary skilled artisan understands from the description herein that these sequences are capable of interfering with replication in cancer either directly or indirectly, including, for example, indirectly mediated by an immune response. From the description provided herein, the ordinary skilled artisan understands the sequences to be targets against replication, rapid replication and lethality. As a result, the ordinary skilled artisan understands that any amino acid sequence comprising any one or more of the sequences of Table 1 (or functional fragments thereof) may be used to directly or indirectly interfere with replication in cancer. The ordinary skilled artisan knows how to isolate or synthesize amino acid sequences that reflect a whole protein, a protein fragment, a polypeptide, or a peptide comprising, consisting essentially of, or consisting of at least one sequence or functional fragment of Table 1 (SEQ ID NO(s): 1-203). The artisan further knows how to use the isolated or synthesized amino acid sequence to target replication in cancer by administering the sequence to a human or animal.

As used herein, the term cancer "type" refers to malignancies that share histology or origin. One of ordinary skill in the art knows how to separate different malignancies by cancer "type." Malignancies subject to aspects of the invention may be of the same cancer type or of different cancer types. The malignancies may also be of unknown type or may be metastatic and of known or unknown type. Many cancers histologically diagnosed in a primary malignancy are of unknown cancer type such as when a metastasis that is being examined has changed and has become difficult or impossible to type by histological methods. In such cases, the present therapeutic compositions provide vaccines across various histological types of cancer.

As used herein, "homologous" or "homology" or "sequence identity" are used to indicate that an amino acid sequence or nucleic acid sequence exhibits substantial structural or functional equivalence with another sequence. Any structural or functional differences between sequences having sequence identity or homology will be de minimus; that is, they will not affect the ability of the sequence to function as indicated in the desired application. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological cross-reactivity, similar enzymatic activity, etc. The ordinary skilled practitioner can readily determine each of these characteristics by art-known methods.

To determine the percent identity or percent homology of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, 90%, 95%, 97%, 99% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences as compared to the total length of the sequence identified as a reference sequence.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991).

As used herein a "vaccine" is any substance, compound, composition, mixture, or other therapeutic substance that, when administered to a human or animal via any method of administration known to the skilled artisan now or hereafter, produces an immune response, a humoral response, an antibody response, a blocking effect, or a protective effect in the human or animal.

A "functional fragment" of a Replikin sequence as described herein is a fragment, variant, analog, or chemical derivative of a Replikin sequence that retains at least a portion of the immunological cross reactivity with an antibody specific for the Replikin sequence. A fragment of the Replikin sequence refers to any subset of the molecule. Variant peptides of the sequence may be made by direct chemical synthesis, for example, using methods well known in the art. An analog of a Replikin sequence to a non-natural protein or polypeptide is substantially similar to either the Replikin sequence of the protein or a fragment thereof. Chemical derivatives of a Replikin sequence contain additional chemical moieties.

As used herein, the term "specifically binds," and related terms referencing the interaction of a binding molecule such as, for example, an antibody, and the structure to which it binds (antigen) means that the binding molecule preferentially recognizes the structure to which it binds even when present among other molecules (such as in a mixture of molecules). Specific binding of a binding molecule to a binding structure or an immunogenic portion of a binding structure is specific when the binding molecule binds to the structure or portion thereof and does not bind with the same level of affinity to other structures. Binding affinity may be determined by one of ordinary skill in the art using, for example, BIACORE, enzyme-linked immunosorbent assays, or radioimmuno assays. A binding molecule may cross-react with related antigens and preferably does not cross-react with affinity to unrelated antigens. Binding between a binding molecule and the structure to which it binds may be mediated by covalent or non-covalent attachment, or both.

Peptides Shared Across Different Histological Types of Cancer

An embodiment of the present invention provides isolated or synthesized peptides shared across differing types of cancer, including different histological types of cancer. Table 1 below provides various Replikin sequences shared among different histological types of cancer and HIV. Sequences residing in the same row and within a box reflect an exact sharing of the sequence among the various histological types (or HIV). The sequences in Table 1 were identified as present in normal (non-cancer) and non-infectious disease genomes in concentrations less than 20 per 100 amino acids (Replikin Count), but in cancer cell genomes in concentrations greater than 20 per 100 amino acids and as high as 324 in glioblastoma multiforme. As a result, each of the sequences in Table 1 is understood to be present in cancer cells of various histological types in high concentrations, not present in non-cancer cells in concentrations higher than 20 (except in viral and bacterial infections where they are associated with degree of lethality of the organism), range as high as 150 or greater, and shared across the various histological types of lethal cancer where the sequence is within a box. The highest genomic concentrations of these sequences were identified in proteins related to cancer with the highest mortality rates.

One embodiment of the present invention provides one or more of the peptides listed in Table 1. Another embodiment provides functional fragments of one or more of the peptides listed in Table 1 as well as peptides sharing percent sequence identity with one or more of the peptides listed in Table 1. Percent sequence identity may be 30%, 40%, 50%, 60%, 70%, 80%, 90%, 95%, 97%, 99%, or more. Peptides sharing percent sequence identity may share functional characteristics.

Another embodiment provides proteins, protein fragments, polypeptides, or other compounds comprising one or more of the peptides listed in Table 1, functional fragments of one or more of the peptides listed in Table 1, or peptides sharing percent identity with one or more peptides or functional fragments of the peptides listed in Table 1.

As may be seen in Table 1, significant numbers of sequences are shared among the various histological cancer types listed in the table. For example, numerous sequences are shared among glioblastoma multiforme, lung cancer, and leukemia. Many of these sequences are also shared with peptides expressed from human immunodeficiency virus (HIV). Numerous other sequences are likewise shared among lung cancer, breast cancer, and HIV. Sequences are also shared among lung cancer and the group of cancers of colon, colorectal, and cervix. Many sequences are also shared among lung cancer, leukemia, and breast cancer and among leukemia and breast cancer and leukemia and lung cancer. Sequences are also shared among pancreatic cancer and the group of colon cancer, colorectal cancer, and cervical cancer. Any sequence that is shared among two or more types of cancer or with HIV is useful for targeting rapid replication across the shared types of cancer and is useful for diagnostic and therapeutic purposes across various types of cancer. Any homologue of a sequence in Table 1 is likewise useful for diagnostic and therapeutic purposes across various types of cancer including across types of cancer shared by the sequence and the homologue of the sequence.

The shared sequences are Replikin sequences. Replikin sequences have been shown to be involved in rapid replication of malignant cells as well as viruses and other pathogens. See, e.g., U.S. application Ser. No. 12/010,027, filed Jan. 18, 2008 and U.S. Pat. No. 7,894,999. The concentration of Replikin sequences in the genome or in a protein or proteins of a malignant cell (as determined by identifying the number of Replikin sequences per 100 expressed amino acid residues) has further been correlated with the five-year mortality rate among major histological types of cancer. See, e.g., Table 2 in Example 4. The inventors' identification of shared Replikin sequences among glioblastoma multiforme, pancreatic cancer, lung cancer, leukemia, colon cancer, colorectal cancer, cervical cancer, breast cancer, and HIV provides peptides for therapeutic and diagnostic purposes in these malignancies and in HIV and malignancies arising in association with HIV infection.

The concentration of these shared peptides relates to lethality. The relationship between Replikin sequences and lethality has been demonstrated in infectious diseases such as influenza, SARS, malaria, West Nile virus, porcine circovirus, taura syndrome virus, foot and mouth disease, and porcine respiratory and reproductive syndrome virus. See, e.g., WO 2008/143717, FIGS. 1-21. It is nevertheless surprising to discover that the sharing of Replikin sequences among various cancer types and the relationship of Replikin sequences to lethality would extend into the field of cancer. A common thread in these discoveries is clearly the relationship of Replikin sequences to rapid replication, whether in viruses, bacteria, or cancer cells. Another common thread is the now-well-established importance of rapid replication to the lethality of these pathogens in their respective hosts. The sharing of Replikin peptides among various cancer types provides the artisan with a surprising tool for targeting rapid replication and lethality where the structures are available in different cancer types and where the structures are specifically associated with lethality across cancer types. The highest lethality and five-year mortality rates are here shown to be related to the genomic concentration of Replikin peptides.

TABLE 1

| Glioblastoma multiforme | Pancreatic Cancer | Lung Cancer | HIV | Leukemia | Colon, Colorectal, and Cervical Cancer | Breast Cancer |
|---|---|---|---|---|---|---|
| khkdkhk (SEQ ID NO: 1) | | khkdkhk (SEQ ID NO: 53) | khkdkhk (SEQ ID NO: 104) | khkdkhk (SEQ ID NO: 149) | | |
| hkhkdkhk (SEQ ID NO: 2) | | hkhkdkhk (SEQ ID NO: 54) | hkhkdkhk (SEQ ID NO: 105) | hkhkdkhk (SEQ ID NO: 150) | | |
| khkdrehrhk (SEQ ID NO: 3) | | khkdrehrhk (SEQ ID NO: 55) | khkdrehrhk (SEQ ID NO: 106) | khkdrehrhk (SEQ ID NO: 151) | | |
| hkdrehrhk (SEQ ID NO: 4) | | hkdrehrhk (SEQ ID NO: 56) | hkdrehrhk (SEQ ID NO: 107) | hkdrehrhk (SEQ ID NO: 152) | | |
| kdrehrhk (SEQ ID NO: 5) | | kdrehrhk (SEQ ID NO: 57) | kdrehrhk (SEQ ID NO: 108) | kdrehrhk (SEQ ID NO: 153) | | |
| hkehkkdk (SEQ ID NO: 6) | | hkehkkdk (SEQ ID NO: 58) | hkehkkdk (SEQ ID NO: 109) | | | |
| kehkkdk (SEQ ID NO: 7) | | kehkkdk (SEQ ID NO: 59) | kehkkdk (SEQ ID NO: 110) | kehkkek (SEQ ID NO: 154) | | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| hkkdkdkdrek (SEQ ID NO: 8) | | hkkdkekdrek (SEQ ID NO: 60) | hkkdkekdrek (SEQ ID NO: 111) | | | |
| kkdkdkdrekskh (SEQ ID NO: 9) | | kkdkekdrekskh (SEQ ID NO: 61) | kkdkekdrekskh (SEQ ID NO: 112) | | | |
| kdkdkdrekskh (SEQ ID NO: 10) | | kdkdkdrekskh (SEQ ID NO: 62) | kdkdkdrekskh (SEQ ID NO: 113) | | | |
| kdkdrekskh (SEQ ID NO: 11) | | kdkdrekskh (SEQ ID NO: 63) | kdkdrekskh (SEQ ID NO: 114) | | | |
| kdrekskh (SEQ ID NO: 12) | | kdrekskh (SEQ ID NO: 64) | kdrekskh (SEQ ID NO: 115) | | | |
| kskhsnsehk (SEQ ID NO: 13) | | kskhsnsehk (SEQ ID NO: 65) | | | | |
| hkdkhkdrehrhk (SEQ ID NO: 14) | | hkdkhkdrehrhk (SEQ ID NO: 66) | hkdkhkdrehrhk (SEQ ID NO: 116) | | | |
| hkmflmldnk (SEQ ID NO: 15) | | | | | | |
| hnvkpecldaynk (SEQ ID NO: 16) | | | | | | |
| hnvkpecleaynk (SEQ ID NO: 17) | | | | | | |
| hpqrplvlkt-gvqftvk (SEQ ID NO: 18) | | | | | | |
| | | hrhkehkkdk (SEQ ID NO: 67) | hrhkehkkdk (SEQ ID NO: 117) | hrhkehkkek (SEQ ID NO: 155) | | |
| | | kgkdyskh (SEQ ID NO: 68) | | | | |
| | | kdkekdrekskh (SEQ ID NO: 69) | kdkekdrekskh (SEQ ID NO: 118) | | | |
| | | kekdrekskh (SEQ ID NO: 70) | kekdrekskh (SEQ ID NO: 119) | | | |
| | | khsnsehk (SEQ ID NO: 71) | khsnsehk (SEQ ID NO: 120) | | | |
| | | hsnsehkdsekkhk (SEQ ID NO: 72) | hsnsehkdsekkhk (SEQ ID NO: 121) | | | |
| | | hkdsekkhk (SEQ ID NO: 73) | hkdsekkhk (SEQ ID NO: 122) | | | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| | | kdsekkhk (SEQ ID NO: 74) | kdsekkhk (SEQ ID NO: 123) | | | |
| | | kkhkekek (SEQ ID NO: 75) | kkhkekek (SEQ ID NO: 124) | | | |
| | | kkhkekektk (SEQ ID NO: 76) | | | | |
| | | khkekek (SEQ ID NO: 77) | khkekek (SEQ ID NO: 125) | khkekrk (SEQ ID NO: 156) | | |
| | | hkekektk (SEQ ID NO: 78) | hkekektk (SEQ ID NO: 126) | | | |
| | | kekektkh (SEQ ID NO: 79) | kekektkh (SEQ ID NO: 127) | | | |
| | | kektkhk (SEQ ID NO: 80) | kektkhk (SEQ ID NO: 128) | | | |
| | | ktkhkdgssek (SEQ ID NO: 81) | ktkhkdgssek (SEQ ID NO: 129) | | | |
| | | khkdgssek (SEQ ID NO: 82) | khkdgssek (SEQ ID NO: 130) | | | |
| | | hkdgssek (SEQ ID NO: 83) | hkdgssek (SEQ ID NO: 131) | | | |
| | | kdgssekh (SEQ ID NO: 84) | kdgssekh (SEQ ID NO: 132) | | | |
| | | hkdkhkdrdk (SEQ ID NO: 85) | hkdkhkdrdk (SEQ ID NO: 133) | | | |
| | | kdkhkdrdk (SEQ ID NO: 86) | kdkhkdrdk (SEQ ID NO: 134) | | | |
| | | khkdrdk (SEQ ID NO: 87) | khkdrdk (SEQ ID NO: 135) | | | |
| | | hkkekdrek (SEQ ID NO: 88) | | hkkekdrek (SEQ ID NO: 157) | | |
| | | kehkkekdrek (SEQ ID NO: 89) | | | | |
| | kaecplckqpfdsifh (SEQ ID NO: 28) | | | | kaecplckqpfdsifh (SEQ ID NO: 166) | |
| | kdeqinkgh (SEQ ID NO: 29) | | | | kdeqinkgh (SEQ ID NO: 167) | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| | hsvlgkd-eqink (SEQ ID NO: 30) | | | | hsvlgkd-eqink (SEQ ID NO: 168) | |
| | knhrkhhgk (SEQ ID NO: 31) | | | | knhrkhhgk (SEQ ID NO: 169) | |
| | khhgkkrmk (SEQ ID NO: 32) | | | | khhgkkrmk (SEQ ID NO: 170) | |
| | hgkkrmksk (SEQ ID NO: 33) | | | | hgkkrmksk (SEQ ID NO: 171) | |
| | kknnhserk (SEQ ID NO: 34) | | | | kknnhserk (SEQ ID NO: 172) | |
| | knnhserk (SEQ ID NO: 35) | | | | knnhserk (SEQ ID NO: 173) | |
| | kpggkrkyk-trh (SEQ ID NO: 36) | | | | kpggkrkyk-trh (SEQ ID NO: 174) | |
| | kakdshyqk (SEQ ID NO: 37) | | | | kakdshyqk (SEQ ID NO: 175) | |
| | kdshyqk (SEQ ID NO: 38) | | | | kdshyqk (SEQ ID NO: 176) | |
| | khkrrkrk (SEQ ID NO: 39) | | | | khkrrkrk (SEQ ID NO: 177) | |
| | katdttkh (SEQ ID NO: 40) | | | | katdttkh (SEQ ID NO: 178) | |
| | khhkkkk (SEQ ID NO: 41) | | | | khhkkkk (SEQ ID NO: 179) | |
| | hhkkkkkkhk (SEQ ID NO: 42) | | | | hhkkkkkkhk (SEQ ID NO: 180) | |
| | hkkkkkkhk (SEQ ID NO: 43) | | | | hkkkkkkhk (SEQ ID NO: 181) | |
| | kkkkkkhk (SEQ ID NO: 44) | | | | kkkkkkhk (SEQ ID NO: 182) | |
| | kkkkkhk (SEQ ID NO: 45) | | | | kkkkkhk (SEQ ID NO: 183) | |
| | kkkkhkk (SEQ ID NO: 46) | | | | kkkkhkk (SEQ ID NO: 184) | |
| | kkkhkkk (SEQ ID NO: 47) | | | | kkkhkkk (SEQ ID NO: 185) | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| | kkhkkkhk (SEQ ID NO: 48) | | | | kkhkkkhk (SEQ ID NO: 186) | |
| | khkkhk (SEQ ID NO: 49) | | | | khkkhk (SEQ ID NO: 187) | |
| | khkkkhk (SEQ ID NO: 50) | | | | khkkkhk (SEQ ID NO: 188) | |
| | khkkkhkkhh (SEQ ID NO: 51) | | | | khkkkhkkhh (SEQ ID NO: 189) | |
| | kghcdsstrik (SEQ ID NO: 52) | kghcdsstrik (SEQ ID NO: 90) | | | kghcdsstrik (SEQ ID NO: 190) | |
| | | hkdrdkek (SEQ ID NO: 91) | hkdrdkek (SEQ ID NO: 136) | | | |
| | | | kehkkek (SEQ ID NO: 137) | kehkkek (SEQ ID NO: 154) | | |
| | | | | hkehkkek (SEQ ID NO: 158) | | |
| | | | kehkhkdhk (SEQ ID NO: 138) | kehkhkdhk (SEQ ID NO: 159) | | kehkhkdhk (SEQ ID NO: 194) |
| | | kwkflehk (SEQ ID NO: 92) | kwkflehk (SEQ ID NO: 139) | kwkflehk (SEQ ID NO: 160) | | kwkflehk (SEQ ID NO: 195) |
| | | kmldheyttk (SEQ ID NO: 93) | kmldheyttk (SEQ ID NO: 140) | kmldheyttk (SEQ ID NO: 161) | | kmldheyttk (SEQ ID NO: 196) |
| | | kvpspppghk (SEQ ID NO: 94) | | kvpspppghk (SEQ ID NO: 162) | | kvpspppghk (SEQ ID NO: 197) |
| | | hkwkevrhdnk (SEQ ID NO: 95) | hkwkevrhdnk (SEQ ID NO: 141) | hkwkevrhdnk (SEQ ID NO: 163) | | hkwkevrhdnk (SEQ ID NO: 198) |
| | | kwkevrhdnk (SEQ ID NO: 96) | kwkevrhdnk (SEQ ID NO: 142) | kwkevrhdnk (SEQ ID NO: 164) | | kwkevrhdnk (SEQ ID NO: 199) |
| | | kevrhdnk (SEQ ID NO: 97) | kevrhdnk (SEQ ID NO: 143) | kevrhdnk (SEQ ID NO: 165) | | kevrhdnk (SEQ ID NO: 200) |
| | | | | | | kfydgkh (SEQ ID NO: 201) |
| | | | | | | hspklekslk (SEQ ID NO: 202) |
| | | hkerianfk (SEQ ID NO: 98) | | | | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| | | khptcpnk (SEQ ID NO: 99) | | | | |
| | | kcnlqyhfk (SEQ ID NO: 100) | | | | |
| | | kkcnlqyhfk (SEQ ID NO: 101) | | | | |
| | | hfprkvytcgk (SEQ ID NO: 102) | | | | |
| | | hdqknhrkhhgk (SEQ ID NO: 103) | | | | |
| | | | kqngfasphik (SEQ ID NO: 144) | | | |
| | | | khrdkdk (SEQ ID NO: 145) | | | khrdkdk (SEQ ID NO: 203) |
| | | | kkhrdkdk (SEQ ID NO: 146) | | kkhrdkdk (SEQ ID NO: 191) | |
| | | | | | hkdhkkdk (SEQ ID NO: 192) | |
| | | | kdkehkhk (SEQ ID NO: 147) | | | |
| | | | | | kykdkehk (SEQ ID NO: 193) | |
| | | | hkkdkerek (SEQ ID NO: 148) | | | |
| klqfhnvk (SEQ ID NO: 19) | | | | | | |
| ketsslyklqfh (SEQ ID NO: 20) | | | | | | |
| hsnllakketsslyk (SEQ ID NO: 21) | | | | | | |
| hraredswlkslfvrk (SEQ ID NO: 22) | | | | | | |
| kketsnlyklqfh (SEQ ID NO: 23) | | | | | | |
| hsnllakketsnlyk (SEQ ID NO: 24) | | | | | | |

TABLE 1-continued

| Glioblastoma multiforme | Pancreatic Cancer | Lung Cancer | HIV | Leukemia | Colon, Colorectal, and Cervical Cancer | Breast Cancer |
|---|---|---|---|---|---|---|
| kslfvrkvdprkdah (SEQ ID NO: 25) | | | | | | |
| kdahsnllak (SEQ ID NO: 26) | | | | | | |
| kdahsnllakket snlyklqfh (SEQ ID NO: 27) | | | | | | |

Shared Peptides in Compositions for Interfering with Replication in Cancer

Compositions for interfering with replication in cancer comprising the sequences of Table 1, polypeptides comprising the sequences, other compounds comprising the sequences, peptides consisting essentially of the sequences, peptides consisting of the sequences, or proteins comprising the sequences are provided to be directed at replication of the various cancers, including rapid replication and lethality. A composition for interfering with replication in cancer may be any composition for interfering with replication. The composition may interfere with replication directly or indirectly. Direct interference with replication may include, for example, interposition of the specific genomic structure of a Replikin sequence into the mechanism of replication of cancer cells. Indirect interference with replication may include, for example, interference mediated by an immune response.

One example of a composition for interfering with replication may be an immunogenic composition comprising any one or more of the sequences of Table 1 or a functional fragment thereof. A composition may include a polypeptide comprising a sequence or sequences, other compounds comprising a sequence or sequences, peptides consisting essentially of a sequence or sequences, peptides consisting of a sequence or sequences, or proteins comprising a sequence or sequences. Such immunogenic compositions are provided to be directed at the presence of the various cancers, including diagnosis, prevention, or treatment of the various cancers. Such compositions, polypeptides, peptides, proteins, and compounds may be used to induce an immune response in an animal, including a human. Antibodies, antibody fragments, or other binding agents directed against such peptides are also provided and may be used to diagnose the presence of cancer in a patient or to provide passive immunity in a patient. Such cancers may include, but are not limited to, glioblastoma multiforme, pancreatic cancer, lung cancer, leukemia, colon cancer, colorectal cancer, cervical cancer, breast cancer, or any other type of cancer, including cancers related to (or metastatic of) glioblastoma multiforme, pancreatic cancer, lung cancer, leukemia, colon cancer, colorectal cancer, cervical cancer, or breast cancer. Such antibodies, antibody fragments, or other binding agents may also be used to diagnose HIV infection and cancer development in patients suffering from HIV. Immunogenicity of Replikin structures is one of several mechanisms by which the Replikin structure interferes with replication is cancer. Other mechanisms include other mechanism for indirect interference and mechanisms for direct interference including interposition of a specific genomic into the mechanism of replication in cancer cells.

Compositions for interfering with replication in cancer may be (or may be comprised within) a vaccine. The vaccine may comprise one or more pharmaceutically-acceptable carriers and/or adjuvants. The vaccine of the invention is effective across the various histological types of cancer and allows medical practitioners to administer one vaccine against more than one type of cancer and allows medical practitioners to administer a vaccine where the histology of a cancer is uncertain but where the cancer is suspected of having arisen as one of the shared histological types against which a particular vaccine is directed.

Peptides Shared Among Lethal Cancers and HIV

One third of deaths from HIV result from cancer that develops in conjunction with the HIV infection. As a result, the identification of Replikin peptides that are shared among HIV and lethal cancers provides diagnostic and therapeutic applications for identifying the development of cancer in HIV, for preventing the development of cancer in patients suffering from HIV, and for treating cancers that have developed in patients suffering from HIV.

The peptides shared among HIV and lethal cancers provide immunogenic compositions for raising binding agents against HIV and lethal cancers that are useful for diagnosing HIV and/or the development of cancer from HIV. The peptides also provide immunogenic compositions for vaccines that are administered prophylactically to prevent the development of lethal cancers in patients suffering from HIV. For example, any one or more of SEQ ID NO(s): 104-108 and 110 may be administered in a vaccine to prevent the development of glioblastoma, lung cancer, or leukemia in a patient suffering from HIV. Any one or more of SEQ ID NO(s): 109, 110, and 113-116 may be administered in a vaccine to prevent the development of glioblastoma or lung cancer in a patient suffering from HIV. Likewise, SEQ ID NO(s): 111 and 112 may be administered in a vaccine to prevent the development of lung cancer in a patient suffering from HIV or glioblastoma in a patient suffering from HIV. Any one or more of SEQ ID NO(s): 117-136 and 139-143, may be administered in a vaccine to prevent the development of lung cancer in a patient suffering from HIV. Any one or more of SEQ ID NO(s): 104-108, 110, 117, 125, 156, 139-142, 154, and 155, may be administered in a vaccine to prevent the development of lung cancer and leukemia in a patient suffering from HIV. SEQ ID NO(s): 138-143 may be administered in a vaccine to prevent the development of breast cancer and leukemia. Additionally, SEQ ID NO: 145 may be administered in a vaccine to prevent the development of breast cancer and SEQ ID NO: 146 may be administered in a vaccine to prevent the development of colon cancer, colorectal cancer, and cervical cancer in a patient suffering from HIV.

A vaccine to prevent glioblastoma, pancreatic cancer, lung cancer, leukemia, colon cancer, colorectal cancer, cervical cancer, and breast cancer in a patient suffering from HIV may comprise one or more of SEQ ID NO(s): 104-148. A vaccine comprising at least one sequence from SEQ ID NO(s): 104-108, at least one sequence from SEQ ID NO(s): 109 and 110, at least one sequence from SEQ ID NO(s): 111 and 112, at least one sequence from SEQ ID NO(s): 113-116, at least one sequence from SEQ ID NO(s): 117-136, at least one sequence from SEQ ID NO(s): 117, 125, and 136, the sequence of SEQ ID NO: 138, at least one sequence from SEQ ID NO(s): 139-143, the sequence of SEQ ID NO: 145, and the sequence of SEQ ID NO: 146 is a vaccine provided against glioblastoma, pancreatic cancer, lung cancer, leukemia, colon cancer, colorectal cancer, cervical cancer, and breast cancer in a patient suffering from HIV. A vaccine comprising at least one sequence from SEQ ID NO(s): 105-108, at least one sequence from SEQ ID NO(s): 109, 110, and 113-115, at least one sequence from SEQ ID NO(s): 117-136, and at least one sequence from SEQ ID NO(s): 139-143 is a vaccine provided against glioblastoma, pancreatic cancer, lung cancer, leukemia, colon cancer, colorectal cancer, cervical cancer, and breast cancer in a patient suffering from HIV. As described above, any sequence shared among more than one type of cancer or among one type of cancer and HIV or any sequence in one type of cancer having a homologue in another type of cancer or in HIV is a sequence provided for a vaccine against the various types of cancer or a vaccine against the various types of cancer in a patient suffering from HIV.

The vaccine may also comprise a mixture of peptides, wherein one or more of the peptides are sequences identified as shared among a first group of histological types of cancer and one of more of the peptides are sequences identified as shared among a second group of histological types of cancer, thereby being effective in treating both the first and second types of cancer. Additionally, one or more of the peptides may be sequences identified as shared among a third or additional groups of histological types of cancer. The vaccine may comprise any one of the sequences discussed above or a functional fragment of any one of the sequences discussed above. The vaccine may likewise comprise proteins or protein fragments comprising the sequences or functional fragments of the sequences discussed above.

Peptides from a Particular Histological Type

As disclosed in Table 1, peptides identified in a specific histological type are particularly useful as immunogenic compounds for development of diagnostics and therapeutics for the specific histological type. The peptides of Table 1 represent Replikin peptides identified in the portion of the genome where the highest concentration of Replikin peptides is identified as present. This portion of the genome is known for a magnified association with rapid replication and lethality. See, e.g., U.S. application Ser. No. 12/010,027, filed Jan. 18, 2008. As a result, peptides from this region are particularly useful in vaccines for targeting the rapid replication mechanism of a malignancy and particularly useful for targeting the rapid replication mechanism of a malignancy of the same type.

Peptides of SEQ ID NO(s): 1-27 are particularly useful for diagnostic and therapeutic purposes against glioma multiforme. Peptides of SEQ ID NO(s): 28-52 are particularly useful for diagnostic and therapeutic purposes against cancer of the pancreas. Peptides of SEQ ID NO(s): 53-103 are particularly useful for diagnostic and therapeutic purposes against cancer of the lung. Peptides of SEQ ID NO(s): 149-165 are particularly useful for diagnostic and therapeutic purposes against leukemia. Peptides of SEQ ID NO(s): 166-193 are particularly useful for diagnostic and therapeutic purposes against cancer of the colon, rectum, and cervix. Peptides of SEQ ID NO(s): 194-203 are particularly useful for diagnostic and therapeutic purposes against cancer of the breast.

Proteins, protein fragments, and polypeptides comprising any one or more of these sequences or functional fragments of these sequences are likewise useful for targeting cancer of the histological type in which they have been identified. Corresponding antibodies and other binding agents as well as corresponding antisense and siRNA nucleic acids are likewise useful.

Peptides Sharing Percent Identity with Sequences of Table 1

The invention provides peptides that share percent identity with the peptides disclosed in Table 1 (SEQ ID NO(s): 1-203). A peptide that shares a percent identity exhibits substantial structural and/or functional equivalence with its reference sequence. A peptide may share 30%, 40%, 50%, 60%, 70%, 80%, 90%, 95%, 97%, 99%, or more identity with any one of SEQ ID NO(s): 1-203. In sharing this percent identity, peptides of the invention share structural and/or functional characteristics and may be used interchangeably with the peptides of SEQ ID NO(s): 1-203.

Certain peptides disclosed in Table 1 as identified in a particular histological cancer type are not disclosed with a corresponding shared peptide in another histological cancer type. Peptides that are not shared in Table 1 include, for example, SEQ ID NO(s): 8, 9, 16-18, 68, 76, 89, 98-103, 144, 147, 148, 155, 156, 158, 192, 193, 201, and 202. Some of these peptides differ by a single peptide from peptides in the same row in Table 1; these peptides include SEQ ID NO(s): 8, 9, 154, 155, and 156. Peptides that share percent identity with SEQ ID NO(s): 8, 9, 15-27, 68, 76, 89, 98-103, 144, 147, 148, 155, 156, 158, 192, 193, 201, and 202 are provided as peptides of the invention. Further, where peptides that share identity with these sequences are identified in different histological types of cancer, the sequences and/or peptides that share percent identity with the sequences are useful for diagnostic and therapeutic purposes for both the histological type in which the sequence was identified in Table 1 and for the histological type in which the sequence sharing identity is identified.

In a further embodiment, the invention provides peptides that share percent identity with any one of SEQ ID NO(s): 1-203 and retain the elements of a Replikin peptide. The elements of a Replikin peptide are an amino acid sequence of 7 to about 50 amino acids with at least one lysine residue located on one end of the sequence and at least one lysine residue or at least one histidine residue located at the other end of the sequence; (1) a first lysine residue located six to ten residues from a second lysine residue; (2) at least one histidine residue; and (3) at least 6% lysine residues. Because Replikin peptides have been shown to be related to rapid replication, a Replikin peptide that shares percent identity with any one of SEQ ID NO(s): 1-203 may be used for diagnostic and therapeutic purposes of the invention including as an immunogenic composition or vaccine against histological types of cancer sharing sequences with the desired percent identity or sequences with exact identity. Further, a Replikin peptide sequence that shares lysine residues and a histidine residue in the same positions as the lysine residues and histidine residue defining the Replikin sequence of SEQ ID NO(s): 1-203 is useful for diagnostic and therapeutic purposes of the invention including as an immunogenic composition or vaccine against histological types of cancer sharing homologues of the sequences. The lysine residues and histidine residue that define a Replikin peptide sequence are key structures for the function of the Replikin sequence in rapid replication.

Peptides Homologous with Previously-Described UTOPES

A review of Table 1 reveals several sequences previously described in U.S. application Ser. No. 10/860,050, filed Jun. 4, 2004 (now U.S. Pat. No. 7,442,761), as universal synthetic epitopes or "UTOPES." Such peptides include SEQ ID NO(s): 44-47 identified in pancreatic cancer and correspondingly shared SEQ ID NO(s): 182-185 identified in colon, colorectal, and cervical cancers. The new and surprising discovery that these sequences are shared between pancreatic cancer and colon, colorectal, and cervical cancers provides the artisan with a new and surprising use of the sequences in immunogenic compositions, including diagnostic applications as well as cancer vaccines. The sequences may additionally be used in diagnostics and therapeutics across histological types. This application of the previously-identified peptides was not previously known and is a surprising application of the sequences.

Peptides Shared Among Endodermal Cancers

An embodiment of the present invention provides isolated or synthesized Replikin peptides identified as shared or as having homologues or peptides sharing percent identity among cancers of endodermal origin. A further embodiment provides a protein, protein fragment, or polypeptide comprising said Replikin peptides or a functional fragment of said Replikin peptides.

As may be seen in Table 1, peptides are shared among the endodermal cancers of the pancreas, lung, colon, rectum, and cervix. Peptides shared among these endodermal cancers are comprised in therapeutic agents against the family of endodermal cancers. These shared peptides are further a basis of diagnostic techniques for identifying endodermal cancers. The invention, therefore, provides proteins, protein fragments, and polypeptides comprising Replikin peptides identified as shared among endodermal cancers. The invention further provides functional fragments of Replikin peptides identified as shared among endodermal cancers. Such peptides may be used to stimulate the immune system to produce antibodies, antibody fragments, or other binding agents that may be used to diagnose endodermal cancers and may be used to provide passive immunity against endodermal cancers.

Peptides Shared Among Ectodermal Cancers

An embodiment of present invention provides isolated or synthesized Replikin peptides identified as shared or as having homologues or peptides sharing percent identity among cancers of ectodermal origin. A further embodiment provides a protein, protein fragment, or polypeptide comprising said Replikin peptides or a functional fragment of said Replikin peptides.

As may be seen in Table 1, peptides of the ectodermal glioblastoma multiforme cancer are provided. Peptides shared between glioblastoma and other ectodermal cancers may be comprised in therapeutic agents against the family of ectodermal cancers. These shared peptides may further be the basis of diagnostic techniques for identifying ectodermal cancers. The invention, therefore, provides proteins, protein fragments, and polypeptides comprising Replikin peptides identified as shared among ectodermal cancers. The invention further provides functional fragments of Replikin peptides identified as shared among ectodermal cancers. Such peptides may be used to stimulate the immune system to produce antibodies, antibody fragments, or other binding agents that may be used to diagnose ectodermal cancers and may be used to provide passive immunity against ectodermal cancers.

Peptides Shared Among Mesodermal Cancers

An embodiment of the present invention provides isolated or synthesized Replikin peptides identified as shared or as having homologues or peptides sharing percent identity among cancers of mesodermal origin. A further embodiment provides a protein, protein fragment, or polypeptide comprising said Replikin peptides or a functional fragment of said Replikin peptides.

As may be seen in Table 1, peptides of mesodermal cancer of the breast are provided. Peptides shared between breast cancer and other mesodermal cancers may be comprised in therapeutic agents against the family of mesodermal cancers. These shared peptides may further be the basis of diagnostic techniques for identifying mesodermal cancers.

The invention, therefore, provides proteins, protein fragments, and polypeptides comprising Replikin peptides identified as shared among mesodermal cancers. The invention further provides functional fragments of Replikin peptides identified as shared among mesodermal cancers. Such peptides may be used to stimulate the immune system to produce antibodies, antibody fragments, or other binding agents that may be used to diagnose mesodermal cancers and may be used to provide passive immunity against mesodermal cancers.

Vaccines Against Multiple Types of Cancer

A review of Table 1 reveals numerous shared sequences among various types of cancer and HIV. Sequences that are shared among different types of cancer may be comprised within a vaccine against these various cancers. Such vaccines may be administered as a preventive or therapeutic agent against any one or more of these cancers. One vaccine provided for two or more histological types of cancer saves production costs, distribution costs, diagnostic costs, therapeutic costs and storage costs.

Vaccines Against Glioblastoma, Lung Cancer, and Leukemia

In considering Table 1, for example, the peptide sequence of SEQ ID NO: 2 identified in glioblastoma multiforme has the same amino acid sequences as SEQ ID NO: 54, identified in lung cancer, and SEQ ID NO: 150, identified in leukemia. Additionally, SEQ ID NO(s): 2, 54, and 150 have the same amino acid sequence as SEQ ID NO: 105, identified in human immunodeficiency virus (HIV). This pattern is also seen in SEQ ID NO(s): 1 and 3-5 of glioblastoma multiforme, SEQ ID NO(s): 53 and 55-57 of lung cancer, SEQ ID NO(s) 149 and 151-153 of leukemia, and SEQ ID NO(s): 104 and 106-108 of HIV, respectively. Additionally, the peptide sequence of SEQ ID NO: 7 identified in glioblastoma multiforme has the same amino acid sequences as SEQ ID NO: 59, identified in lung cancer, and SEQ ID NO: 110, identified in HIV. The peptide sequence of SEQ ID NO(s): 7, 59, and 110 differ from the amino acid sequence of SEQ ID NO: 154, identified in leukemia in that SEQ ID NO: 154 has a glutamic acid instead of an aspartic acid as the second position from the N-terminus.

One or more of each of these peptides may be comprised in a vaccine directed against the various cancer types of glioblastoma multiforme, lung cancer, or leukemia. Each of these peptides may further be comprised in a vaccine for the prevention of these cancers in patients suffering from HIV or in a vaccine against existing cancers in a patient suffering from HIV.

Immunogenic or Therapeutic Agents Combining Two or More Peptides

Another embodiment of the invention provides immunogenic and/or therapeutic agents comprising two or more of the peptides of the invention, including, for example, the peptides listed in Table 1 or peptides sharing percent identity with the peptides listed in Table 1. Such immunogenic and/or therapeutic agents provide the medical practitioner with a vaccine or other agent effective against multiple cancer types, as necessary. As a result, the medical practitioner may use an embodiment of the invention where more than one histological cancer type is present, where the histology of the cancer is unknown, or where the histological type of cancer is a match for the types of cancer against which the vaccine or other therapeutic agent was designed.

In another embodiment, the invention contemplates a protein, protein fragment, polypeptide, or other compound comprising two or more of the peptides listed in Table 1 as an immunogenically-active agent of the protein, protein fragment, polypeptide or other compound. The invention further provides a composition comprising one or more proteins, protein fragments, polypeptides, or other compounds, wherein each of said proteins, protein fragments, polypeptides, or other compounds comprises at least one of the peptides listed in Table 1.

Replikin Sequences in Diagnostics and Therapies

Because Replikin sequences are chemically defined, they may be synthesized by organic chemistry or biological techniques. Replikin sequences synthesized by organic chemistry may be particularly specific, highly reproducible, and highly reliable as compared to other vaccines and therapies. Chemically-defined Replikin sequences are likewise potentially freer from adverse reactions characteristic of biologically-derived vaccines and antibodies.

An embodiment of an aspect of the invention provides use of Replikin peptides as immunogenic compositions and provides construction of immunogenic compositions as vaccines, including vaccines that provide an immune response, vaccines that provide a humoral immune response, vaccines that provide an antigenic immune response, vaccines that provide a blocking effect, and vaccines that provide a protective effect.

A Replikin peptide, protein or protein fragment comprising said peptide or functional fragment of said peptide may be used for the manufacture of a medicament for the treatment of malignancy that share said Replikin peptide or that share homologues or peptides of percent identity of said Replikin peptide.

Antibodies Against Replikin Sequences in Diagnostics and Therapies

An embodiment of one aspect of the present invention provides binding molecules, including antibodies, to Replikin peptides and functional fragments of the invention. A binding molecule, antibody, or antibody fragment directed against a Replikin peptide may be used for diagnostic, therapeutic, and/or preventive purposes in cancer, including any cancer known to one of ordinary skill in the art now and hereafter, which may include any cancer of Table 1 as well as a thyroid malignancy, a prostate malignancy, a breast malignancy, a urinary bladder malignancy, a uterine corpus malignancy, a uterine cervix malignancy, a colon malignancy, an ovarian malignancy, a malignancy of the oral cavity, a lymphocytic leukemia malignancy, a multiple myeloma malignancy, a gastric malignancy, a non-small cell lung carcinoma malignancy, a glioblastoma malignancy, or any other malignancy of an animal or a human.

One embodiment of an aspect of the invention provides a method of stimulating the immune system of any animal or human capable of an immune response by administering at least one Replikin peptide or protein fragment comprising at least one Replikin peptide or functional peptide fragment of the invention. Another embodiment provides a method of making an antibody or an antibody fragment that binds to at least one Replikin peptide, at least one protein fragment comprising at least one Replikin peptide, one protein comprising at least one Replikin peptide, or one functional fragment of said at least one Replikin peptide. One of ordinary skill in the art knows myriad ways of making binding molecules, antibodies, antibody fragments, or other binding agents that bind to a Replikin peptide or functional fragment or protein or protein fragment comprising said peptide or functional fragment.

Replikin sequences as agents for stimulating the immune system against cancer are supported by data demonstrating a protective effect from Replikin peptides administered orally to shrimp challenged with taura syndrome virus. See, e.g., U.S. application Ser. No. 12/108,458, filed Apr. 23, 2008. In that study, the effectiveness of completely synthetic Replikin sequences against taura syndrome virus in shrimp (providing 91% protection) suggests a blocking mechanism of action in the shrimp rather than a classical immunological effect since classical antibodies are believed to be weak or absent in shrimp. See, also, antisense nucleic acid and siRNA below for further discussion of blocking mechanisms.

Production and Administration of Vaccines and Other Therapeutics

A peptide vaccine of the invention may include a single Replikin peptide sequence or protein fragment comprising said Replikin peptide sequence or may include a plurality of Replikin sequences shared among various histological malignancies or not shared among various histological malignancies. A vaccine may include a conserved Replikin peptide or peptides in combination with a Replikin peptide or Replikin peptides in a particular malignancy or may be based on other Replikin peptide sequences such as UTOPES. See U.S. Pat. No. 7,442,761. Replikin peptides can be synthesized by any method, including chemical synthesis or recombinant gene technology, and may include non-Replikin sequences. Vaccine compositions of the invention may also contain a pharmaceutically-acceptable carrier and/or adjuvant.

The vaccines of the present invention can be administered alone or in combination with chemotherapies, hormone therapies or other anti-cancer therapies and/or treatments. The vaccine of the present invention may be administered to any animal capable of producing antibodies in an immune response or to any animal capable of producing a humoral response, a blocking effect, a protective effect, or any immune or immune-like response. For example, the vaccine of the present invention may be administered to a mouse, a rat, a rabbit, a chicken, a pig, a human, or any other animal capable of producing an immune response and/or antibodies in response to an antigen or capable of experiencing a blocking effect from administration of the vaccine. Because of the universal nature of Replikin sequences, a vaccine of the invention may be directed at a range of malignancies.

The Replikin peptides of the invention, alone or in various combinations are administered to a subject by any manner known to one of ordinary skill in the art including by intravenous or intramuscular injection, ocular swab or spray, nasal spray and/or inhalation spray, or any other method of administration in order to stimulate the immune system of the subject to produce an immune response or in order to provide a direct or otherwise indirect blocking effect. Generally the dosage of peptides is in the range of from about 0.1 µg to about 10 mg, about 10 µg to about 1 mg, and about 50 µg to about 500 µg. The skilled practitioner can readily determine the dosage and number of doses needed to produce an effective immune response or an effective blocking effect, or both.

In another aspect of the invention, isolated Replikin peptides may be used to generate antibodies, which may be used, for example, to provide passive immunity in an individual. See, e.g., U.S. Pat. No. 7,894,999, filed Feb. 16, 2006 and U.S. application Ser. No. 12/010,027, filed Jan. 18, 2008 (each incorporated herein by reference in their entireties).

Anti-Sense Nucleic Acids and siRNA

An embodiment of one aspect of the invention provides a nucleic acid sequence that is antisense to a nucleic acid that encodes for a Replikin peptide of SEQ ID NO(s): 1-203. Nucleic acid sequences include, for example, one or more small interfering nucleic acid sequences that interfere with a nucleic acid sequence sharing 50%, 60%, 70%, 80%, or 90% or more identity with a nucleic acid that encodes for a Replikin peptide identified in a malignancy or identified as shared among two or more malignancies, or sharing 50%, 60%, 70%, 80%, or 90% or more identity with a nucleic acid that is antisense to a nucleic acid that encodes for a Replikin peptide identified in a malignancy or identified as shared among two or more malignancies.

Such nucleotide sequences may be used in hybridization assays of biopsied tissue or blood, e.g., Southern or Northern analysis, including in situ hybridization assays, to diagnose the presence of a particular malignancy or virus in a tissue sample or an environmental sample, for example. The present invention also contemplates kits containing antibodies or other binding molecules specific for particular Replikin sequences that are present in a particular malignancy of interest, or containing nucleic acid molecules (sense or antisense) that hybridize specifically to a particular Replikin sequence, and optionally, various buffers and/or reagents needed for diagnosis.

Also within the scope of the invention are oligoribonucleotide sequences that include antisense RNA and DNA molecules and ribozymes that function to inhibit the translation of Replikin-containing mRNA. Both antisense RNA and DNA molecules and ribozymes may be prepared by any method known in the art. The antisense molecules can be incorporated into a wide variety of vectors for delivery to a subject. The ordinary skilled practitioner can readily determine the best route of delivery. Intravenous or intramuscular delivery is one possible method of delivery and is one, among many, routine delivery methods in the art of small molecule delivery. The dosage amount is also readily ascertainable. Dosage may range from 0.01 mg to 10 mg, from 0.1 mg to 5 mg, from 0.5 mg to 2 mg, and from 0.75 mg to 1.25 mg, but is not limited to such ranges.

One embodiment of an aspect of the invention further contemplates antisense nucleic acid molecules that are complementary to a nucleic acid encoding a portion of a cell of a malignancy. An antisense nucleic acid molecule may be complementary to a nucleotide sequence encoding a Replikin peptide as described herein. A nucleic acid sequence may be anti-sense to a nucleic acid sequence that has been demonstrated to be conserved in a malignancy or generally conserved in a range of malignancies of a particular cancer type or of different cancer types.

The invention also contemplates compositions comprising RNAi-inducing entities used to inhibit replication of a malignancy including small interfering RNA, which is a class of about 10 to about 50, and often about 20 to about 25, nucleotide-long double-stranded RNA molecules. siRNA is involved in the RNA interference pathway, where it interferes with the expression of one or more specific genes such as replication genes of a malignancy including replication genes that comprise at least one Replikin peptide as described herein. siRNAs also act in RNAi-related pathways, e.g., as an anti-replication mechanism.

An effective amount of an RNAi-inducing entity is delivered to a cell or organism prior to, simultaneously with, or after diagnosis of a malignancy or a metastasis. A dosage should be sufficient to reduce or delay replication of the malignancy or metastasis. Compositions of the invention may comprise a single siRNA species targeted to a target transcript or may comprise a plurality of different siRNA species targeting one or more target transcripts.

The invention provides a small interfering nucleic acid sequence that is about 10 to about 50 nucleic acids in length and is 50%, 60%, 70%, 80%, or 90% or more homologous (or sharing sequence identity) with a nucleic acid that encodes for any portion of at least one Replikin peptide, or is 50%, 60%, 70%, 80%, or 90% or more homologous (or sharing sequence identify) with a nucleic acid that is antisense to a nucleic acid that encodes for any portion of at least one Replikin peptide. In a further non-limiting embodiment, the nucleic acid sequence is about 15 to about 30 nucleic acids or about 20 to about 25 nucleic acids. In a further non-limiting embodiment, the nucleic acids sequence is about 21 nucleic acids.

The inventors provide the following examples for illustration purposes. The ordinary skilled artisan understands the invention encompasses all practices inferable from the examples and the disclosure and data provided in this application. The invention is not limited to the examples or the disclosure provided herein.

Example 1

Identification of Peptides Shared Among Various Histological Types of Cancer and Comprisable in Vaccines Against Said Various Cancers The inventors examined genomic information of various histological types of cancer to determine the region of highest concentration of encoded Replikin peptide sequences. The goal of the examination was to identify Replikin sequences available as synthetic Replikin cancer vaccines for each individual histological type. The inventors were surprised to identify many Replikin peptide sequences within the region of highest concentration of encoded Replikin peptides that were shared among two or more histological types. Because the identified peptides share the requirements of a Replikin sequence, they are structures that are associated with rapid replication. See, e.g., U.S. Pat. Nos. 7,176,275, 7,420,028, 7,763,705, 7,674,880, 7,189,800, 7,758,863, 7,705,129, 7,452,963, 7,442,761, 7,774,144, and 7,894,999, each of which is incorporated herein by reference. Rapid replication in association with Replikin peptides is characteristic of lethal infectious diseases as well as lethal cancers, regardless of histological type. See, e.g., U.S. Pat. Nos. 7,176,275, 7,894,999, and U.S. application Ser. Nos. 12/010,027 and 12/108,458. The number of Replikins per one hundred genomic amino acids (known as Replikin Count) has been found to relate quantitatively to five-year mortality rate. See, e.g., U.S. application Ser. No. 12/538,027.

When the inventors investigated the genomic sites of the highest concentration of Replikin peptides (highest Replikin Count) for specific Replikin sequences to be the basis of a wholly-synthetic Replikin cancer vaccine, the inventors were expecting to identify sequences for a single vaccine for each histological type of cancer. The inventors were, however, surprised to discover that many individual Replikin structures were shared in two or more of the most lethal histological types of cancer, including glioblastoma multiforme, pancreatic cancer, lung cancer, leukemia, colon cancer, colorectal cancer, cervical cancer, and breast cancer. The Replikin structures were furthermore not necessarily found in the same genomic region but were nevertheless identified in the part of the genome of each specific cancer type having the highest concentration of encoded Replikin sequences. This is the region wherein Replikin structures are shown to be magnified in their relationship to rapid replication and lethality. This discovery allowed the inventors to develop single vaccines against more than one of the lethal cancers.

The inventors designed many different vaccines, including but not limited to (1) vaccines against glioblastoma multiforme, lung cancer, leukemia, and cancer in HIV, (2) vaccines against lung cancer, leukemia, and breast cancer, and (3) vaccines against pancreatic cancer, colon cancer, colorectal cancer, and cervical cancer.

Example 2

Replikin Formulation Against Glioblastoma, Lung Cancer, Leukemia, and Cancers Associated with HIV Using the sequences identified in Table 1, the inventors designed a formulation against glioblastoma multiforme, lung cancer, leukemia, and cancer in HIV. The formulation comprises, as interfering peptides, SEQ ID NO(s): 1-5. Each of these sequences is shared among glioblastoma multiforme, lung cancer, leukemia, and HIV.

The inventors designed another formulation against glioblastoma multiforme, lung cancer, leukemia, and cancer in HIV. The formulation comprises, as interfering peptides, SEQ ID NO(s): 1-5 as well as SEQ ID NO(s): 6-14. These sequences are further shared by glioblastoma, lung cancer, and/or HIV. The formulation may also comprise SEQ ID NO: 154, which is a homologue of SEQ ID NO: 7 and shares 86% identity with SEQ ID NO: 7 because SEQ ID NO: 154 shares 6 of seven amino acid residues with SEQ ID NO: 7. SEQ ID NO: 154 is identified in leukemia in Table 1 and, because it is a homologue of SEQ ID NO: 7 in glioblastoma, SEQ ID NO: 59 in lung cancer and SEQ ID NO: 110 in HIV, SEQ ID NO: 154 is useful for targeting rapid replication in leukemia, glioblastoma, lung cancer, and cancer in patients suffering from HIV.

The Replikin formulation is tested in rabbits to determine immunogenicity and in mice and WISTAR rats to determine protective effect, both before cancers are implanted in the animals, and at different intervals after the cancer is implanted. There are numerous protocols for such testing well described in the literature. The following are two such protocols.

In a xenograft model investigation, eight to ten mice female nu/nu mice (eight to nine weeks old) are implanted subcutaneously or in the flank with carcinoma cells. Tumors are monitored (twice weekly and then daily) to determine when the tumor neoplasms reach approximately 75 mg. Animals are pair-matched according to tumor size in the 62- to 126-mg range. Tumor weight is estimated. A tumor growth delay method is used where a test animal is euthanized if tumor size reaches 2.0 g. Animal weight is determined twice weekly and animals are examined frequently for clinical signs of adverse side effects. Acceptable toxicity is defined as no mean group weight loss over 20% during test period, and not more than one toxic death among ten treated animals. Test compositions are formulated in 0.5% methylcellulose and administered per os, intranasally, or subcutaneously in a volume of 10 ml/kg.

In an intracranial survival model investigation, a therapeutic composition is tested for controlling progression of intracranial cancer. For study of intracranial cancer progression, malignant cells are harvested during logarithmic growth phase, suspended in PBS, and injected beneath the skull. 20 microliters is injected into female nu/nu mice at eight to nine weeks of age. Animals are monitored for tumor progression. Survival is the efficacy measurement for the model and is recorded as time to endpoint or death. Moribund animals are euthanized and included in the data as death. Improved life span is calculated as a percentage of controls. Cells are implanted and animals observed for one day for clinical signs of tumor progression. Treatment is then begun. Animals are treated with the composition for fifty days and the study ends at 58 days.

Example 3

Replikin Formulation Against Pancreatic Cancer, Colon Cancer, Colorectal Cancer, and Cervical Cancer Using the sequences identified in Table 1, the inventors designed a Replikin formulation against pancreatic cancer, colon cancer, colorectal cancer, and cervical cancer. The formulation comprises, as interfering peptides, SEQ ID NO(s): 28, 30-36, and 38-42. Each of these sequences is shared among pancreatic cancer, colon cancer, colorectal cancer, and cervical cancer. Alternatively, the formulation comprises, as interfering peptides, SEQ ID NO(s): 28-52.

The formulation is tested in rabbits to determine immunogenicity and in mice and WISTAR rats to determine protective effect. The composition is tested according to the xenograft model investigation described in Example 2.

Example 4

Comparing Relative Lethality of Cancer Cells, Tissues, or Types

The data in Table 2 below demonstrate a quantitative relationship between: (1) Replikin Count in the Replikin Peak Gene of the genome of common types of human cancer; and (2) The five-year mortality in that cancer as reported in Brenner, H., "Long-term survival rates of cancer patients achieved by the end of the 20th century: a period analysis," *The Lancet*, 360 (Oct. 12, 2002), 1131-1135. The discovery of the relation of Replikin sequences to rapid replication as reflected in Table 2 offers a new approach and provides means to inhibit rapid replication and resulting lethality in cancers in animals and humans. To the inventors' knowledge, no structure of cancer cells and no genomic structure of cancer cells has previously been shown to relate quantitatively to the five-year mortality rate of a particular histological type of cancer.

TABLE 2

| Human Cancer Type | 5-Year Percent Mortality of Human Cancer Type | Highest Replikin Count of Replikin Peak Gene |
|---|---|---|
| Thyroid | 2 | 15 |
| Prostate | 3 | 20 |
| Breast | 11 | 45 |
| Urinary Bladder | 15 | 53 |
| Uterine Corpus | 30 | 24 |
| Uterine Cervix | 34 | 31 |

TABLE 2-continued

| Human Cancer Type | 5-Year Percent Mortality of Human Cancer Type | Highest Replikin Count of Replikin Peak Gene |
|---|---|---|
| Colon | 39 | 28 |
| Ovary | 40 | 60 |
| Oral Cavity | 43 | 53 |
| Lymphocytic Leukemia | 58 | 128 |
| Multiple Myeloma | 70 | 170 |
| Gastric | 76 | 92 |
| Non-Small Cell Lung Carcinoma | 92 | 250 |
| Pancreatic | 95 | 275 |
| Glioblastoma | 99 | 324 |

Overall, the data in Table 2 provide an illustration of a quantitative relationship between Replikin concentration in a given type of cancer and lethality in that type of cancer as compared to the Replikin concentration and lethality in other types of cancer. The data in Table 2 also provide further support for a general association between Replikin concentration and lethality within a particular type of cancer (such as, for example, lung cancer) as described in U.S. patent application Ser. No. 12/010,027, filed Jan. 18, 2008.

The association seen in Table 2 is surprising to one of ordinary skill in the art because the Replikin Count in these disparate human malignancies is quantitatively related to mean five-year mortality of sufferers of the specific histological types of malignancy—even though mortality outcomes are significantly dependent upon multiple variables including time of detection and efficacy of disparate treatments. Despite the expected significant differences in time of detection and efficacy of treatment across the population surveyed by Brenner (*Lancet* 2002) and the number of variables that affect outcomes in these cancers, it is quite surprising that the Replikin concentration in these different human malignancies emerges as such a significant variable that quantitatively relates to the mean mortalities reported therein.

As previously stated, to the inventor's knowledge no structure of cancer cells, and no genomic structure of cancer cells, has previously been shown to relate quantitatively to the five-year mortality rate of a particular histological type of cancer cell. Since the specific Replikin genomic sequence structures of cancer cells were not previously known, it was not possible to select such structures for the purpose of interfering with the replication process of the cancer cell. Since some of these newly-discovered sequences are shared between some histological types of cancer, a single formulation can be used for more than one type of cancer, thus making administration of such formulations more practical in that a broader group of specific histological types of cancer cell targets can be addressed by a single formulation.

What is claimed is:

1. A method of stimulating the immune system of a subject against cancer comprising administering an immunogenic composition that comprises a mixture of at least two peptides, wherein each of said two peptides consists of a sequence selected from a group consisting of SEQ ID NO: 6-13 and SEQ ID NO: 14 and a pharmaceutically acceptable carrier.

2. The method of claim 1, wherein said immunogenic composition comprises a mixture of at least each of nine peptides consisting of a sequence of SEQ ID NO(s): 6-14.

3. The method of claim 1, wherein the immune system of a subject is stimulated against cancer in a patient infected with HIV.

4. The method of claim 1, wherein the immune system of a subject is stimulated against one or more of glioblastoma multiforme, lung cancer, and leukemia.

5. The method of claim 4, wherein the immune system of said subject is stimulated at least against glioblastoma multiforme cancer.

6. The method of claim 4, wherein the immune system of said subject is stimulated at least against lung cancer.

7. The method of claim 4, wherein the immune system of said subject is stimulated at least against leukemia and wherein the mixture comprises SEQ ID NO: 7.

* * * * *